United States Patent
Iida et al.

(10) Patent No.: US 9,084,985 B2
(45) Date of Patent: Jul. 21, 2015

(54) METHOD FOR PRODUCING ALICYCLIC CARBOXYLIC ACID AND CATALYST USED IN SAME

(75) Inventors: Akifumi Iida, Niigata (JP); Ryoko Watanabe, Niigata (JP); Tomoo Tsujimoto, Niigata (JP)

(73) Assignee: MITSUBISHI GAS CHEMICAL COMPANY, INC., Tokyo (JP)

( * ) Notice: Subject to any disclaimer, the term of this patent is extended or adjusted under 35 U.S.C. 154(b) by 67 days.

(21) Appl. No.: 14/002,602

(22) PCT Filed: Feb. 24, 2012

(86) PCT No.: PCT/JP2012/054640
§ 371 (c)(1),
(2), (4) Date: Aug. 30, 2013

(87) PCT Pub. No.: WO2012/117976
PCT Pub. Date: Sep. 7, 2012

(65) Prior Publication Data
US 2013/0338393 A1    Dec. 19, 2013

(30) Foreign Application Priority Data

Mar. 1, 2011 (JP) ................... 2011-043523
Jan. 20, 2012 (JP) ................... 2012-010130

(51) Int. Cl.
| | |
|---|---|
| *C07C 51/36* | (2006.01) |
| *B01J 23/63* | (2006.01) |
| *B01J 21/04* | (2006.01) |
| *B01J 23/46* | (2006.01) |
| *B01J 21/06* | (2006.01) |
| *B01J 21/08* | (2006.01) |
| *B01J 21/18* | (2006.01) |
| *B01J 37/02* | (2006.01) |

(52) U.S. Cl.
CPC ............... *B01J 23/462* (2013.01); *B01J 21/04* (2013.01); *B01J 21/063* (2013.01); *B01J 21/066* (2013.01); *B01J 21/08* (2013.01); *B01J 21/18* (2013.01); *B01J 23/63* (2013.01); *B01J 37/0201* (2013.01); *C07C 51/36* (2013.01)

(58) Field of Classification Search
None
See application file for complete search history.

(56) References Cited

FOREIGN PATENT DOCUMENTS

| | | |
|---|---|---|
| CN | 1689698 | 11/2005 |
| CN | 101450308 | 6/2009 |
| JP | 2002 20346 | 1/2002 |
| JP | 2006 45166 | 2/2006 |
| JP | 2006 124313 | 5/2006 |
| JP | 3834836 | 10/2006 |
| JP | 2008 63263 | 3/2008 |
| JP | 2009 40717 | 2/2009 |
| JP | 4622406 | 2/2011 |
| TW | 200400939 A | 1/2004 |
| WO | WO 2004/046078 A1 | 6/2004 |

OTHER PUBLICATIONS

Thomas, J.M et al., "High-Performance Nanocatalysts for Single-Step Hydrogenations", Accounts of Chemical Research, vol. 36, No. 1, pp. 20-30, (2003).
Low-Pressure Hydrogenation of Some Benzenepolycarboxylic Acids with rhodium Catalyst, Journal of Organic Chemicatry, vol. 31, pp. 3438-3439, (1966).
Maegawa, T. et al., "Efficient and Practical Arene Hydrogenation by Heterogeneous Catalysts under Mild Conditions", Chemistry a European Jouranl, vol. 15, pp. 6953-6963, (2009).
"Handbook of Heterogeneous Catalytic Hydrogenation for Organic Synthesis" p. 387.
International Search Report Issued May 29, 2012 in PCT/JP12/054640 Filed Feb. 24, 2012.
Written Opinion of the International Searching Authority Issued May 29, 2012 in PCT/JP12/054640 Filed Feb. 24, 2012.
Extended European Search Report issued Jul. 2, 2014 in Patent Application No. 12752352.0.
Combined Office Action and Search Report issued Apr. 3, 2014 in Taiwanese Application No. 101106711.
Chinese Office Action and Search Report issued Jun. 26, 2014 in Patent Application No. 201280021585.4 with English Translation of Category of Cited Documents.

*Primary Examiner* — Yevegeny Valenrod
(74) *Attorney, Agent, or Firm* — Oblon, McClelland, Maier & Neustadt, L.L.P.

(57) ABSTRACT

Provided is a method for producing an alicyclic carboxylic acid by hydrogenating an aromatic ring of an aromatic carboxylic acid, which comprises using a catalyst containing ruthenium and palladium as a catalyst, and also provided is a co-supported ruthenium-palladium catalyst in which ruthenium and palladium are present in a form of particles containing both the ruthenium and palladium on a surface of a support. A catalyst has been developed which uses a relatively inexpensive noble metal, ruthenium, which has an activity equivalent to that of a rhodium catalyst, and which does not undergo decrease in activity as observed in a rhodium catalyst, and thereby an industrially simple method for producing an alicyclic carboxylic acid has been established.

5 Claims, 28 Drawing Sheets

ANALYZED FIELD(×1000K)

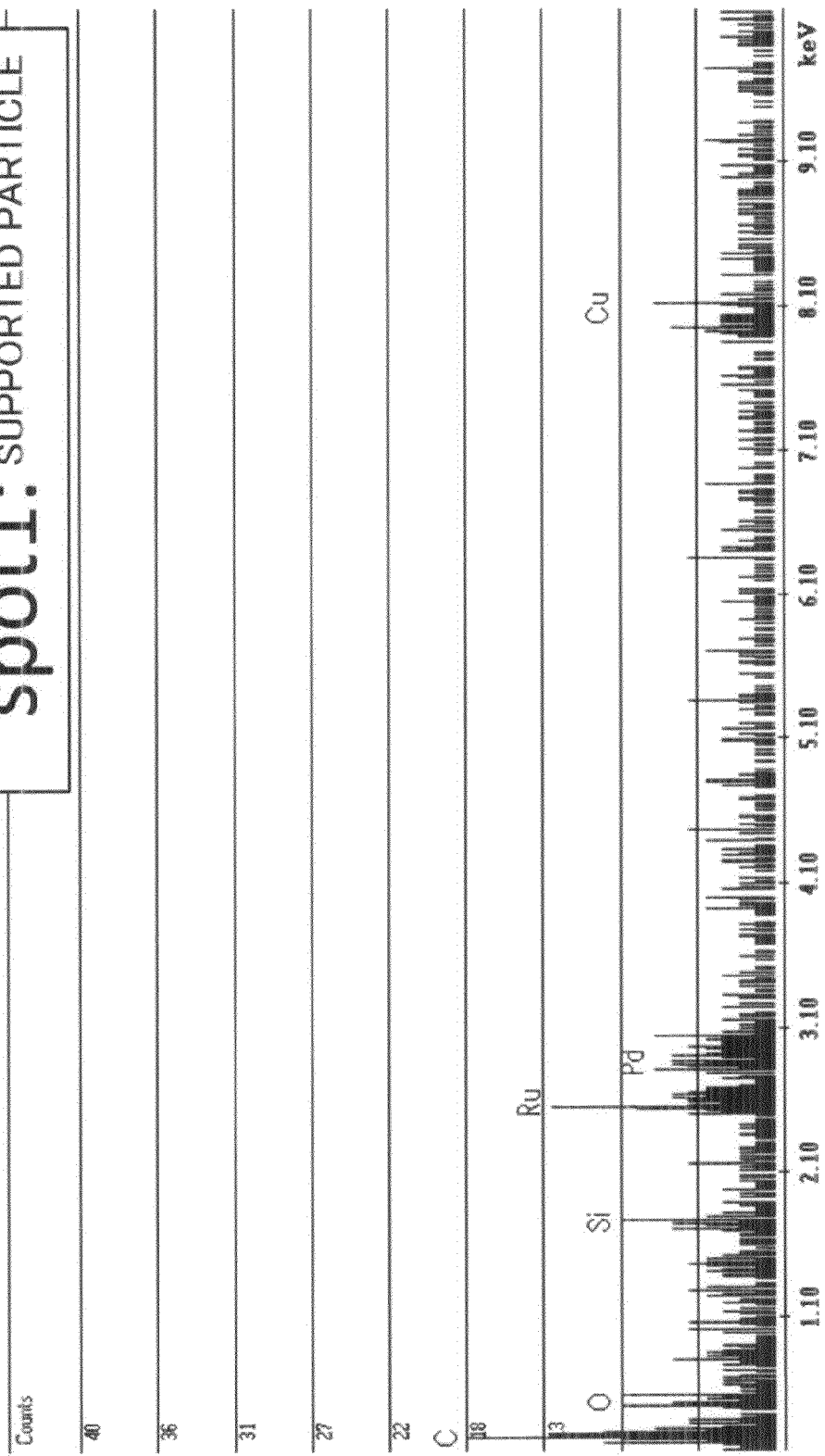

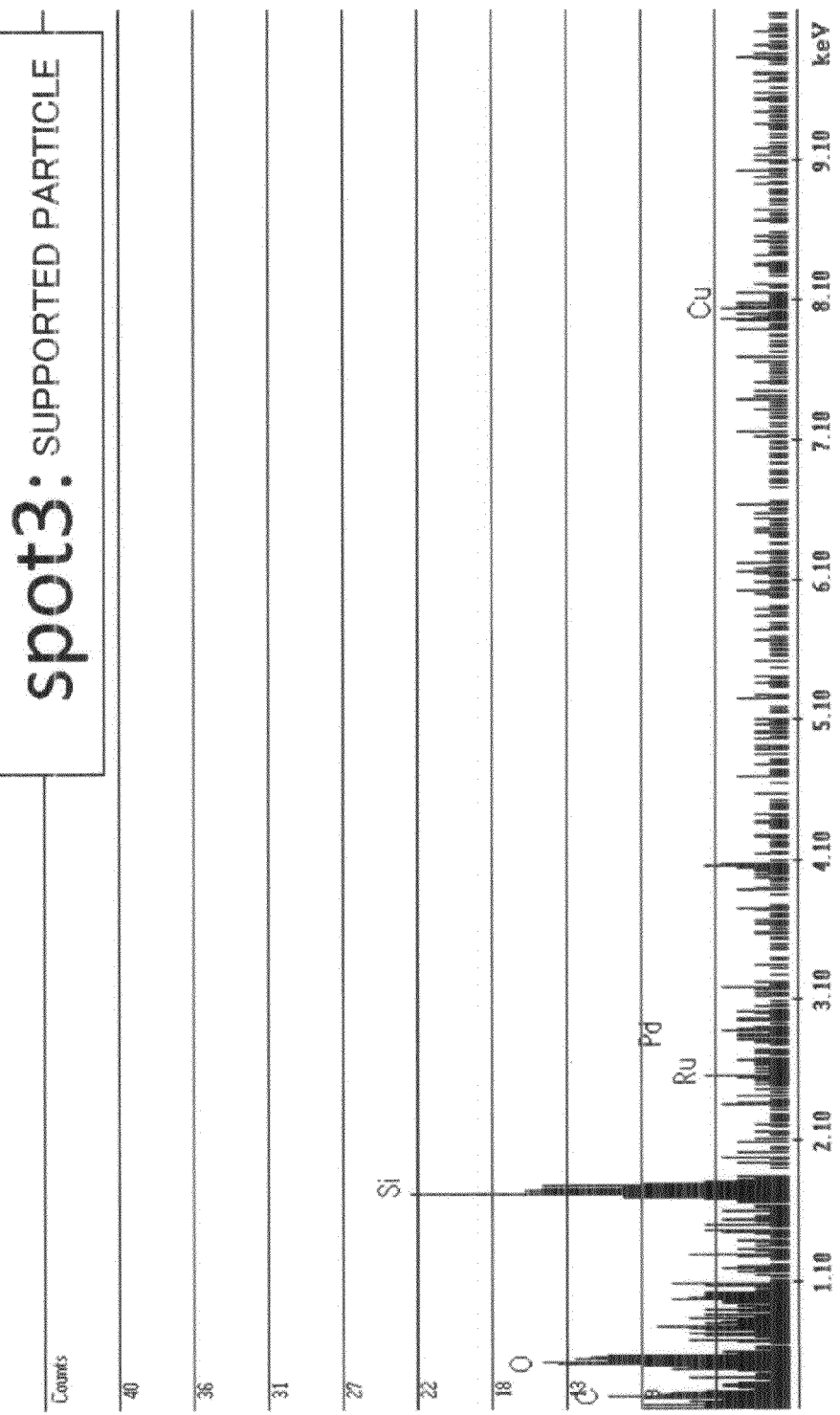

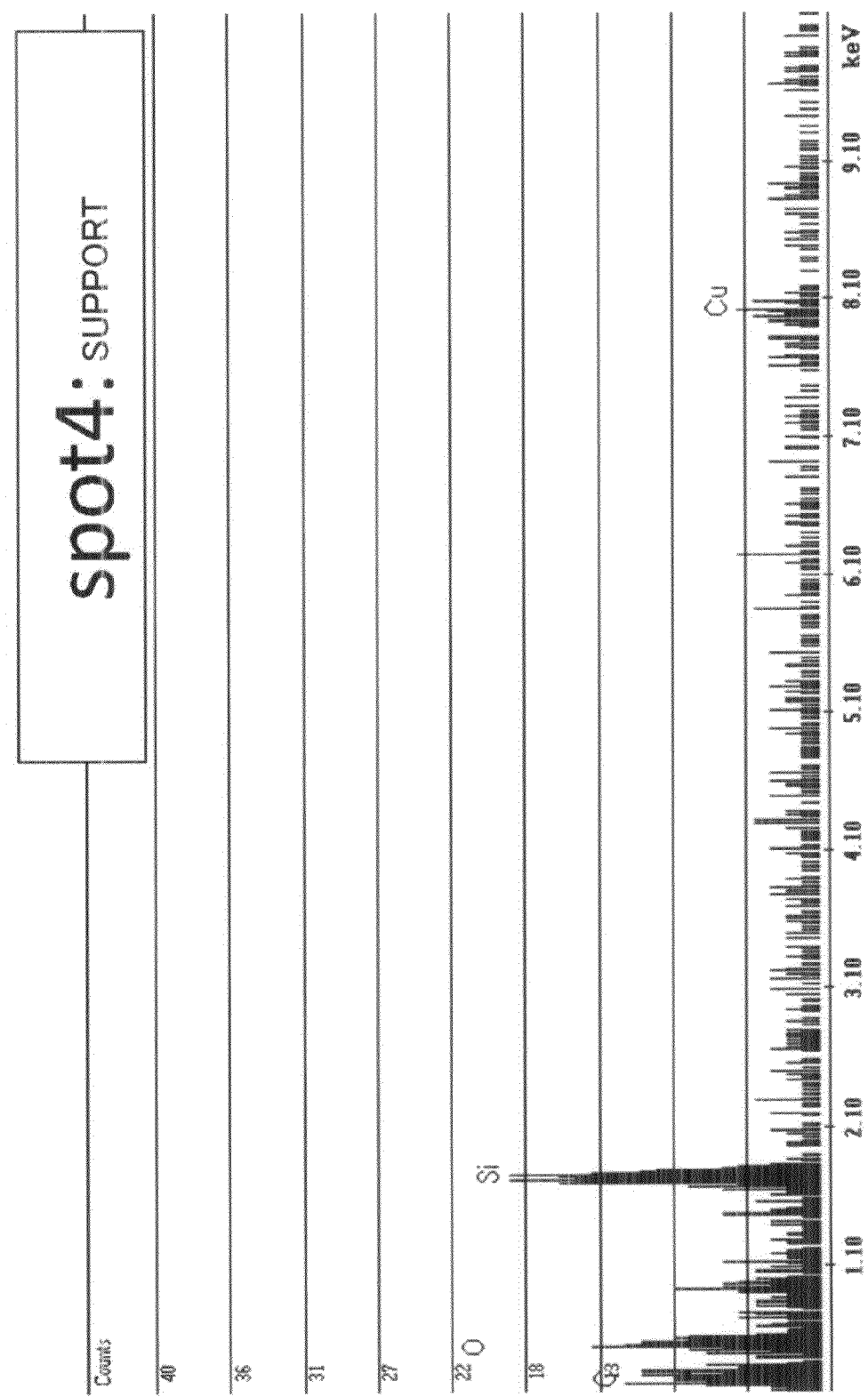

ANALYZED FIELD(×1000K)

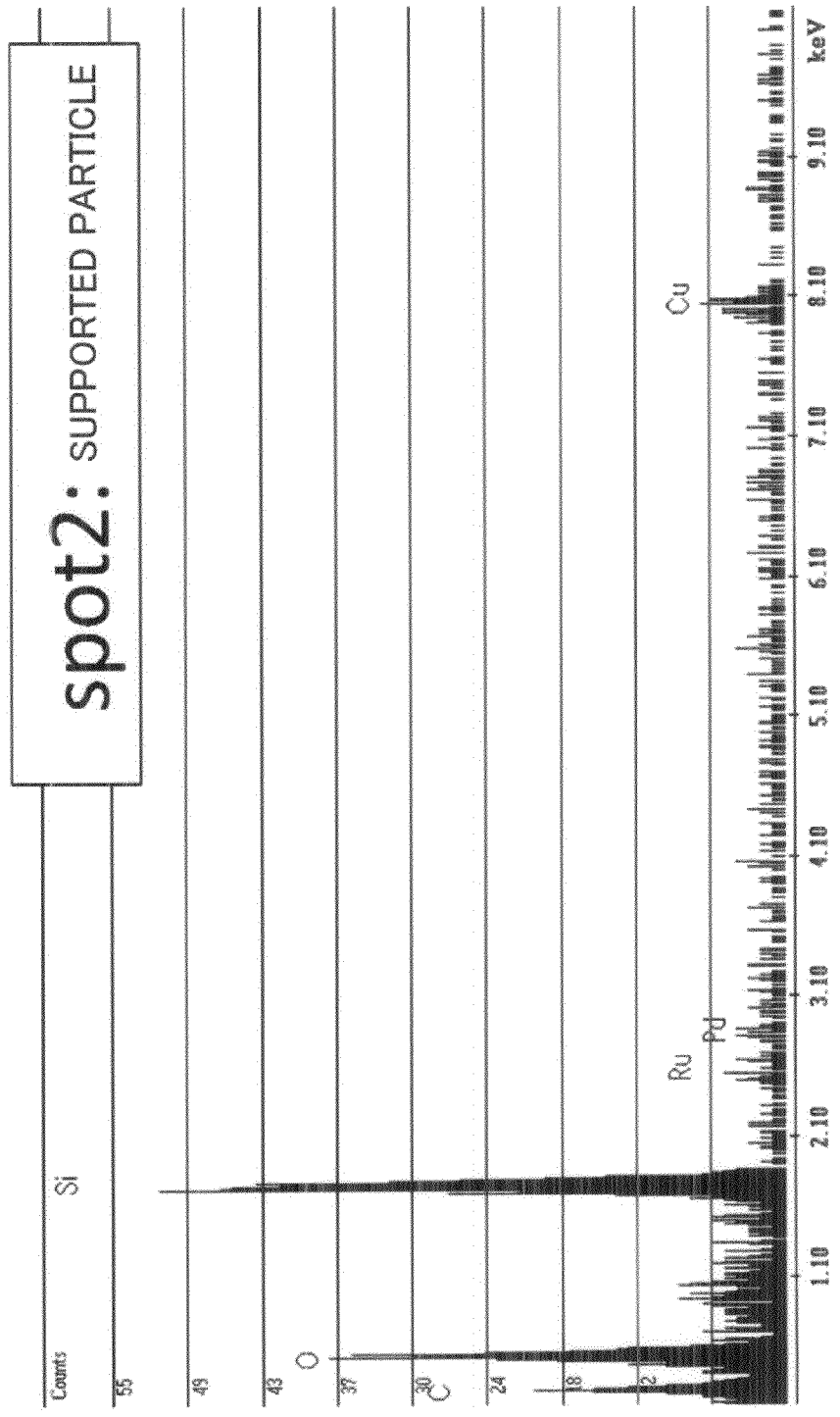

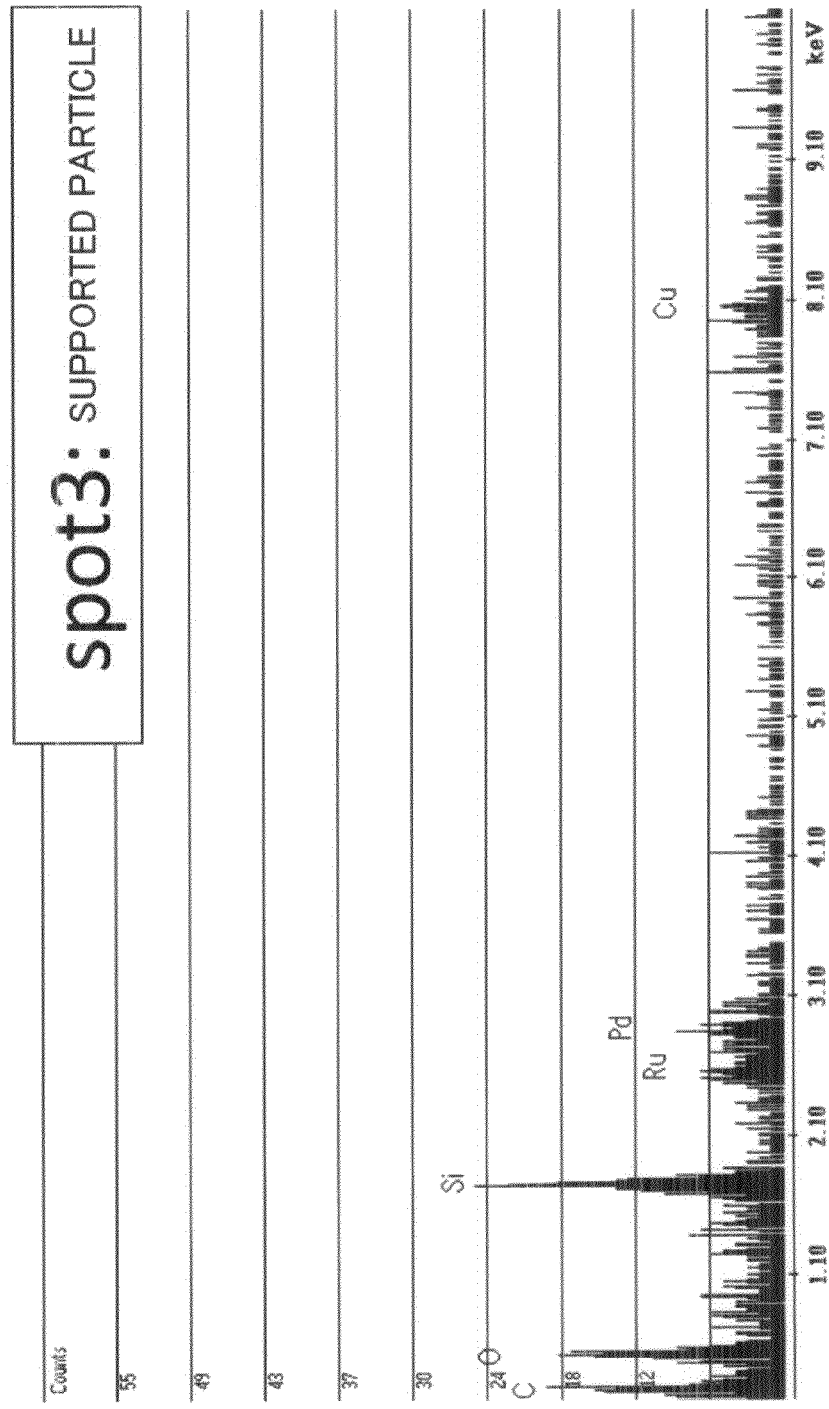

ANALYZED FIELD(×1000K)

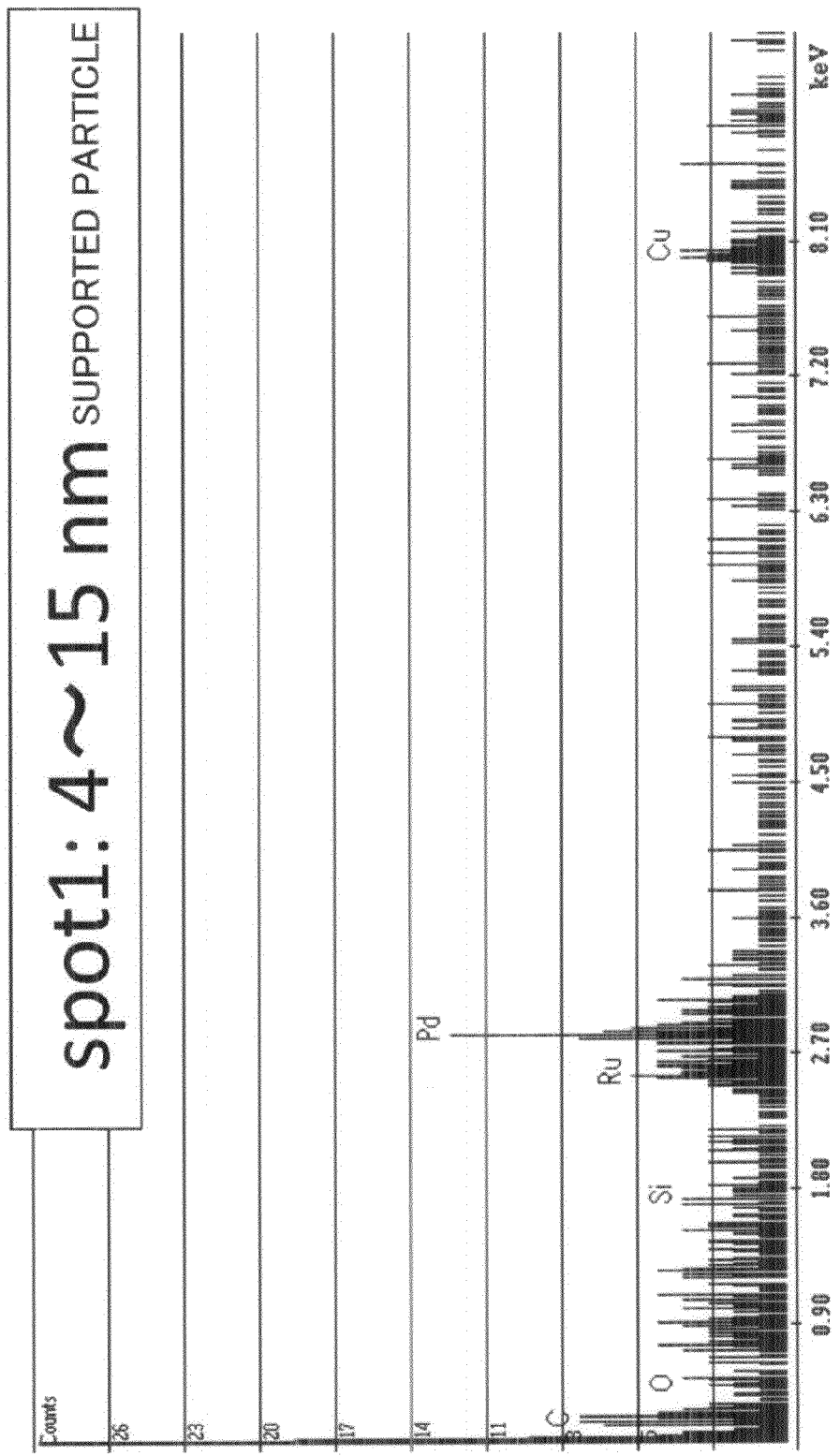

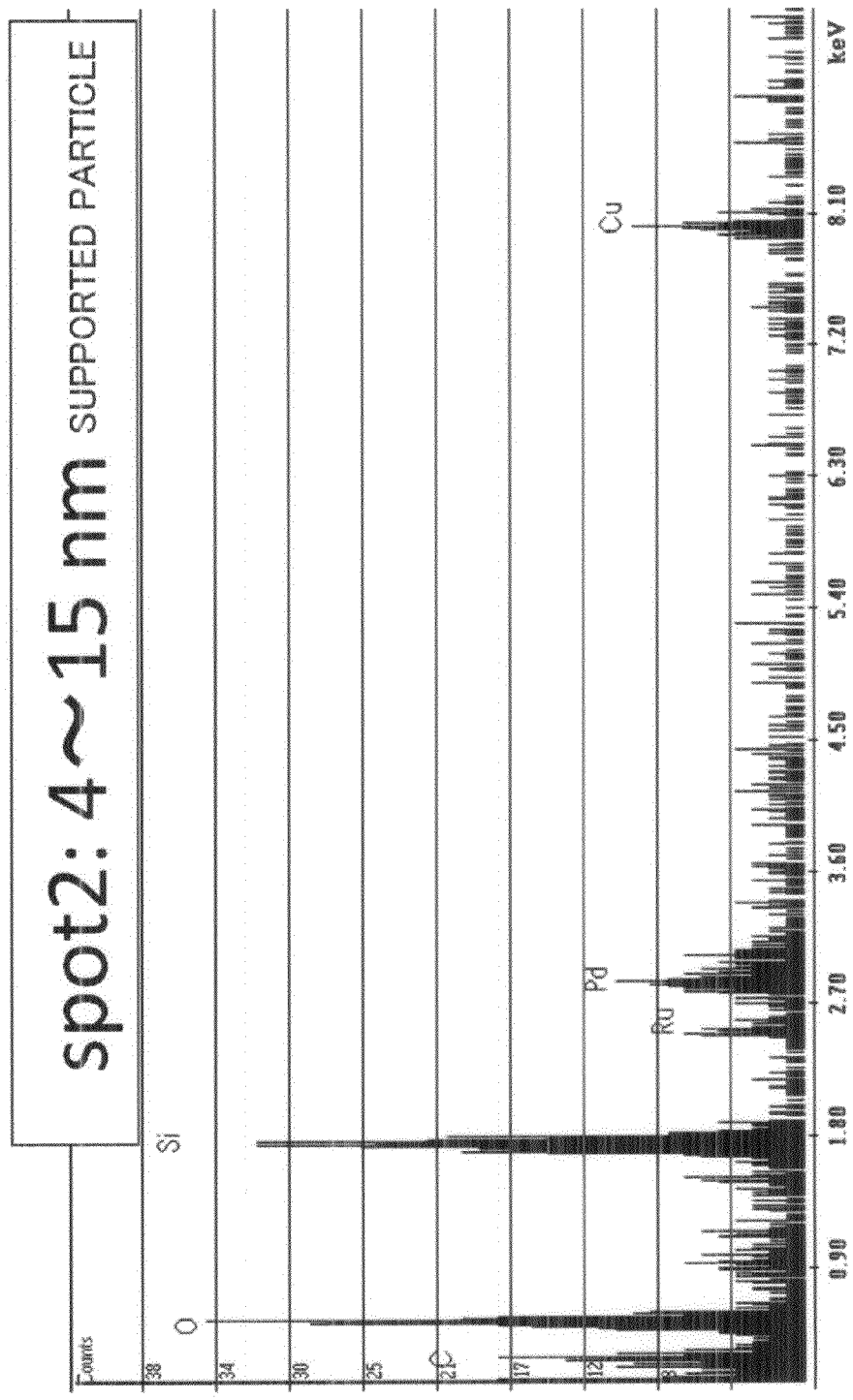

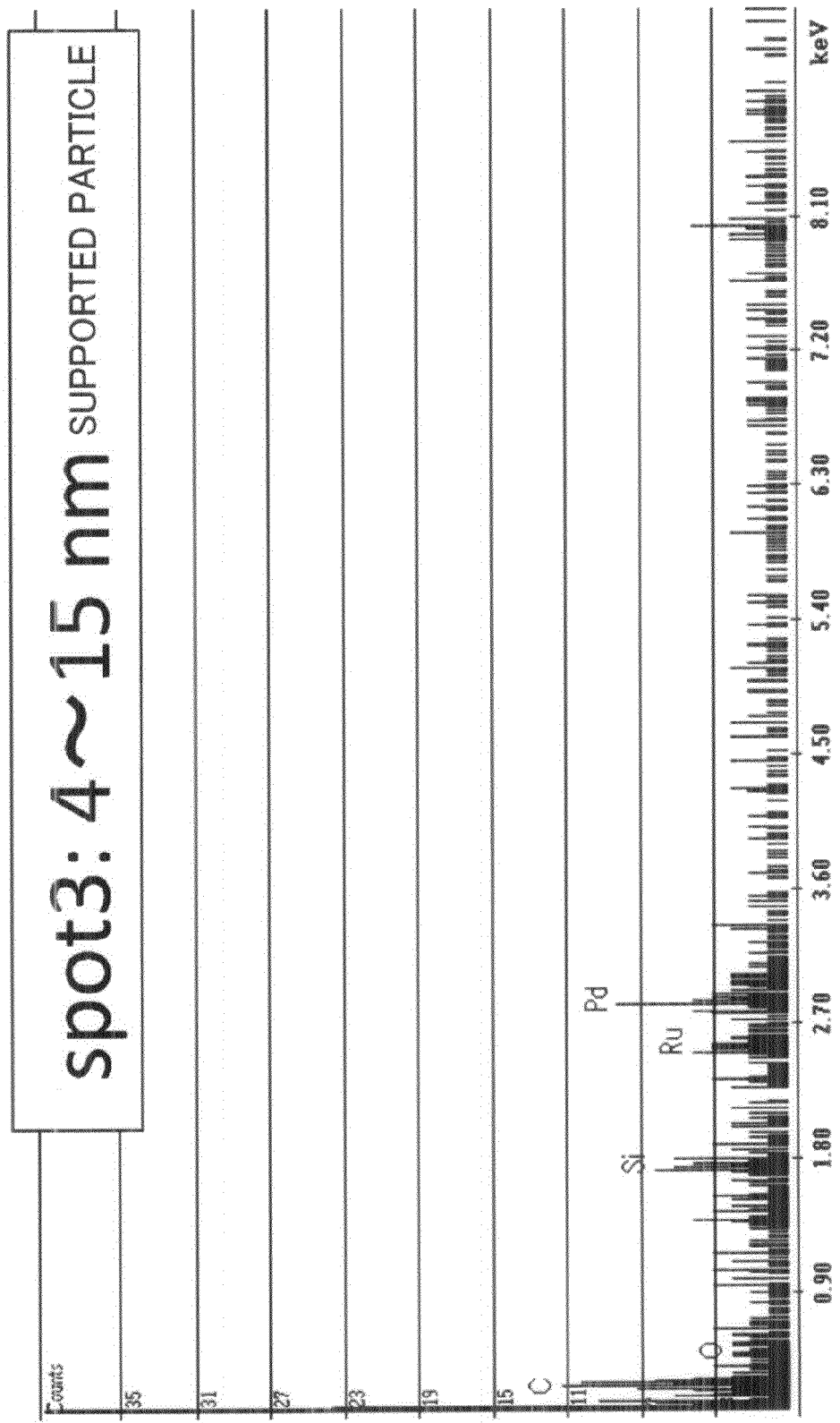

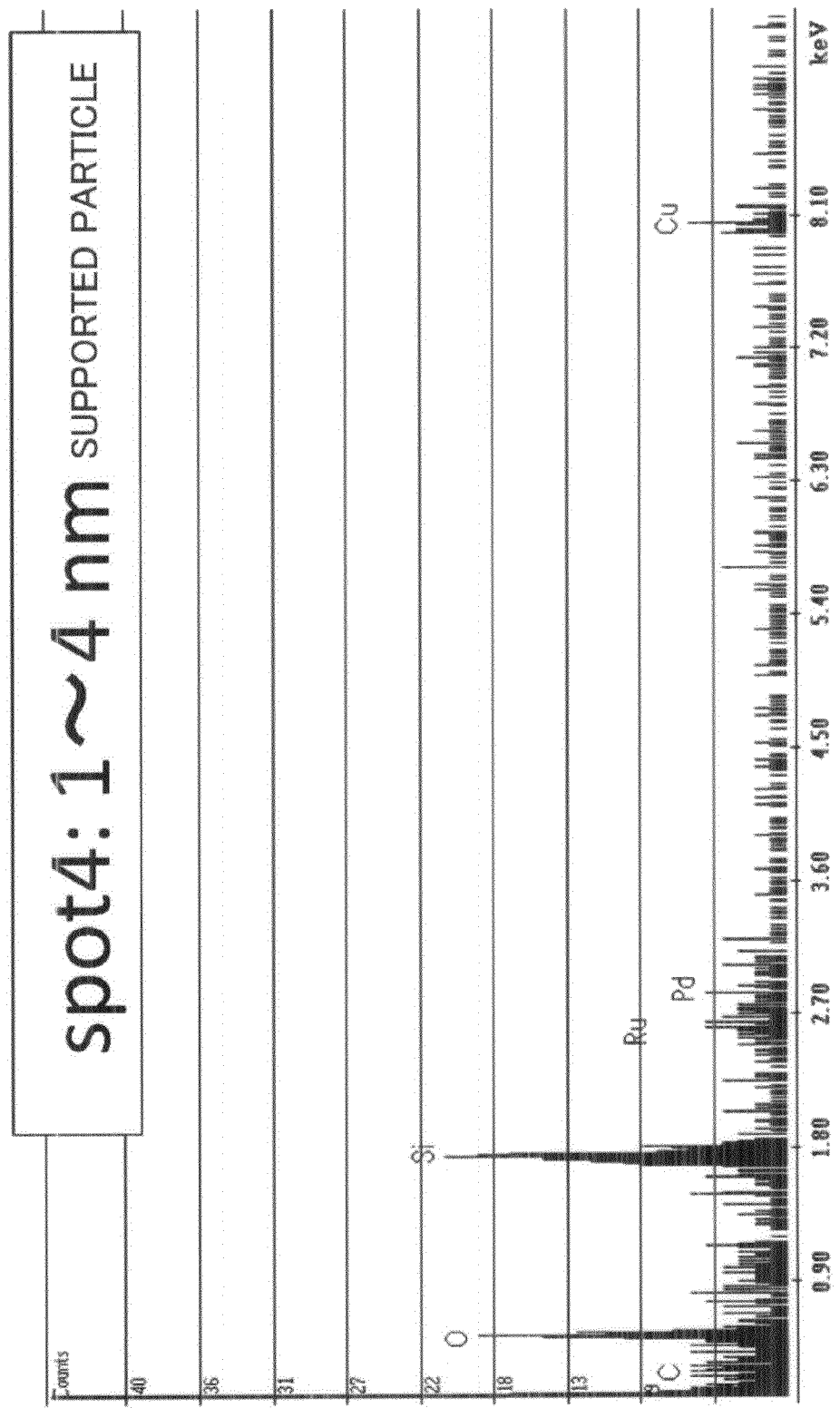

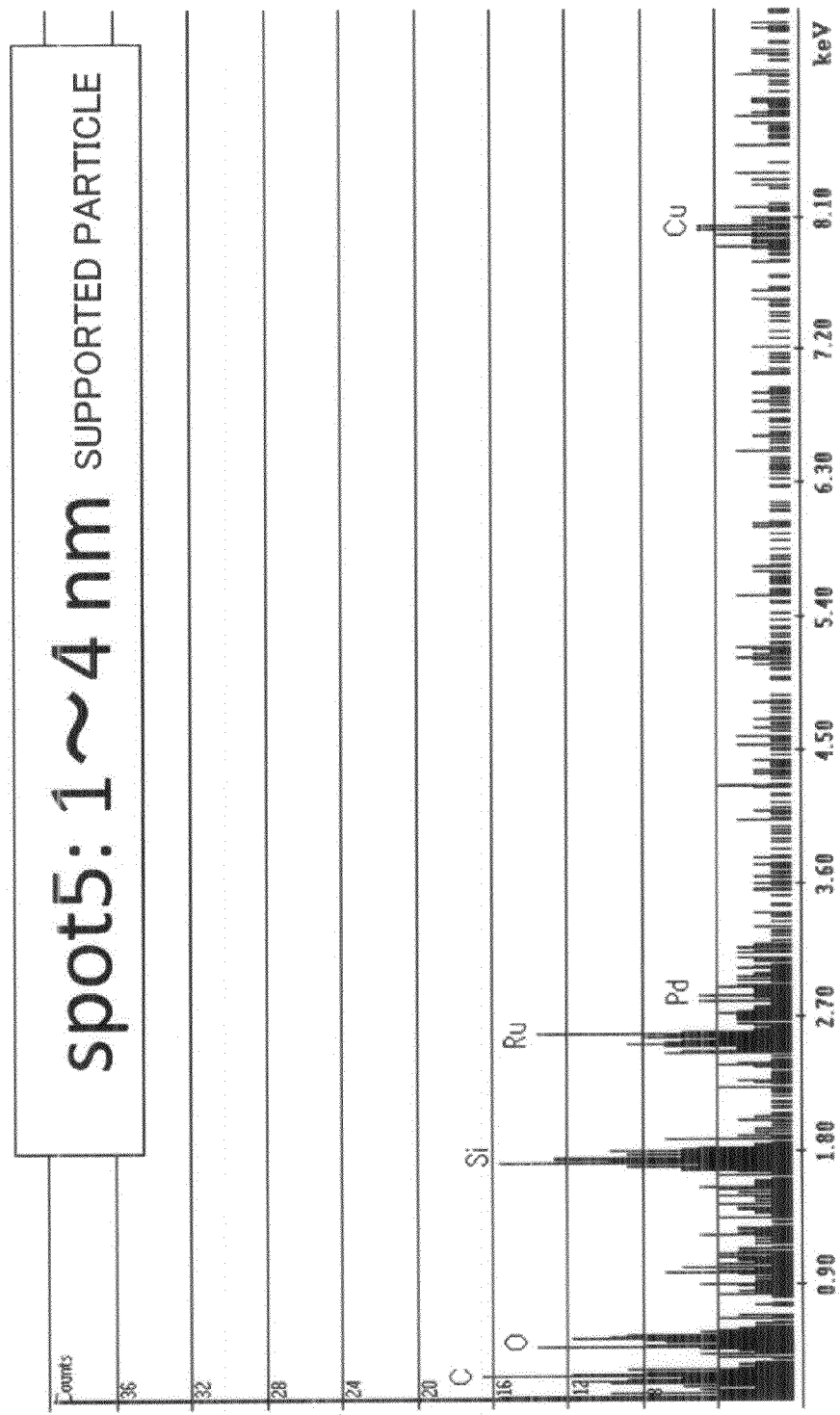

ANALYZED FIELD(×1000K)

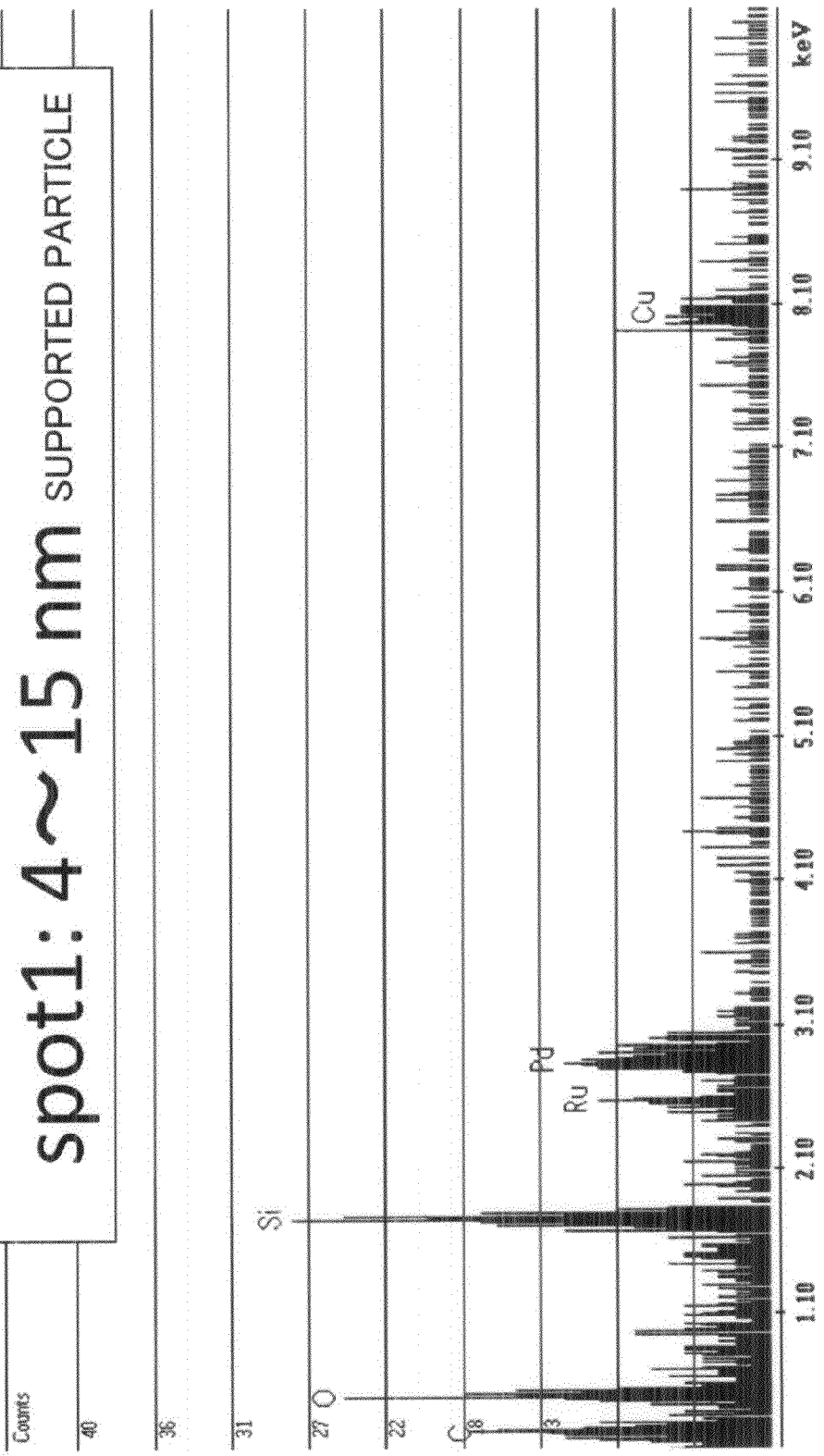

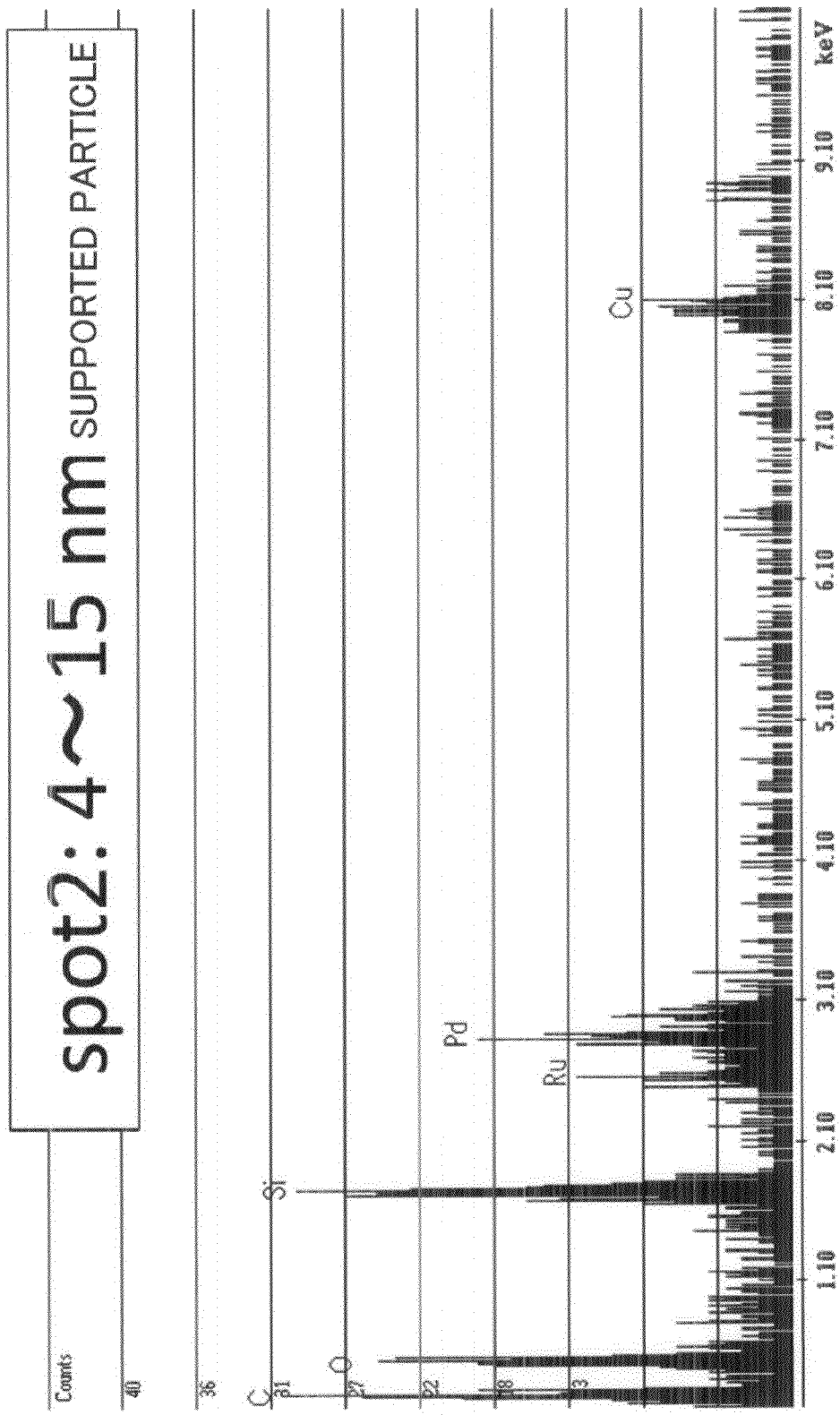

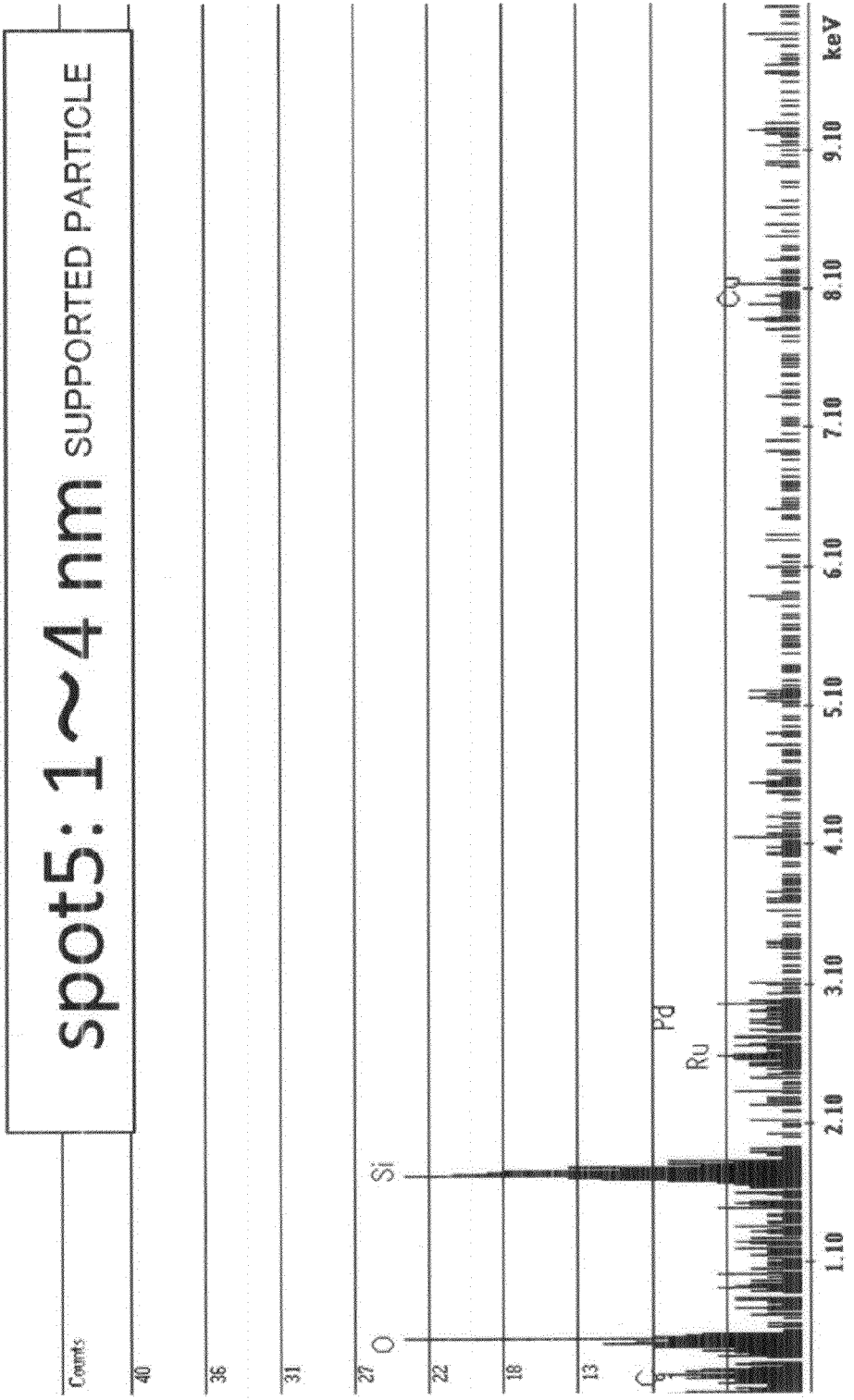

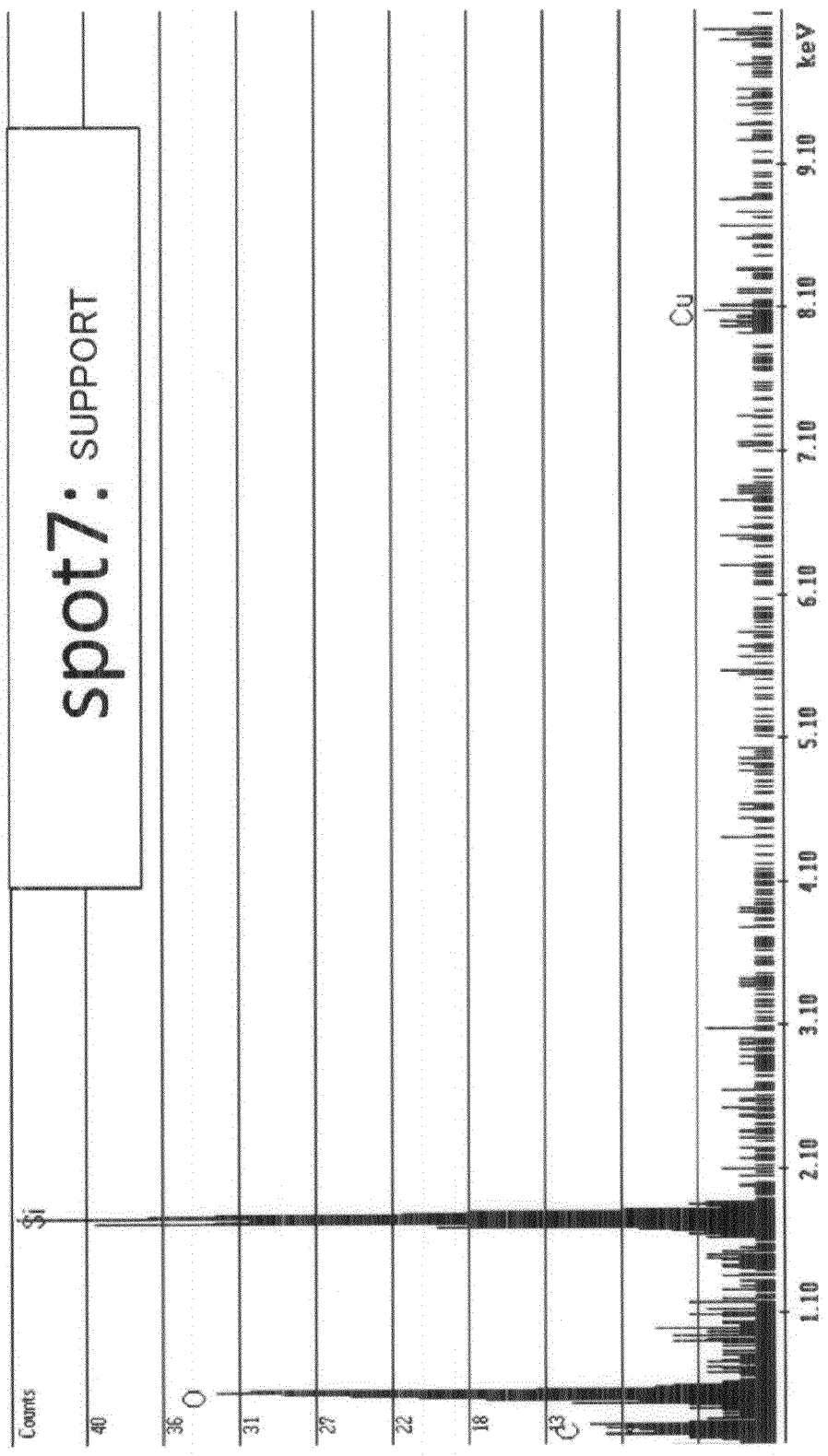

METHOD FOR PRODUCING ALICYCLIC CARBOXYLIC ACID AND CATALYST USED IN SAME

TECHNICAL FIELD

The present invention relates to a method for producing an alicyclic carboxylic acid and a catalyst for hydrogenating an aromatic ring of an aromatic carboxylic acid, the catalyst being suitably usable in the method. Specifically, the present invention relates to a method for producing an alicyclic carboxylic acid by hydrogenating an aromatic carboxylic acid in the presence of a noble metal catalyst. In addition, the catalyst of the present invention is specifically a hydrogenation catalyst in which ruthenium and palladium are co-supported, wherein ruthenium and palladium are present in a form of particles containing both ruthenium and palladium on a surface of a support, in other words, ruthenium and palladium coexist in every single particle.

BACKGROUND ART

Many studies have been made so far on methods for hydrogenating an aromatic carboxylic acid in the presence of a noble metal catalyst, and catalysts used in the methods. Now, regarding a method for directly hydrogenating an aromatic ring of an aromatic carboxylic acid, many studies are being made on rhodium catalysts with which the hydrogenation reaction proceeds under mild conditions (Non Patent Literature 1, Non Patent Literature 2, Patent Literature 1, and Patent Literature 2). Rhodium catalysts have advantages such as a high activity as a catalyst for hydrogenating an aromatic carboxylic acid and a high selectivity to a product without occurrence of any side reaction. Rhodium has such excellent catalytic performances, but has several problems in industrial use. A first problem is its very high price, and this imposes a heavy load of initial investment in the catalyst for industrial use. A second problem is that the degradation speed of the activity of the catalyst is so high that frequent activation operation is required for long-term use of the catalyst. Although a process incorporating activation can be created, a simpler process is desired for industrial use (Patent Literature 1).

Ruthenium is one of the inexpensive noble metals having an ability to hydrogenate an aromatic carboxylic acid. It is generally known that when a ruthenium catalyst is used for hydrogenating an aromatic carboxylic acid, not only hydrogenation of the aromatic ring occurs, but also reduction of the carboxyl group as the side chain occurs. Hence, the selectivity to an alicyclic carboxylic acid decreases. Also from the fact that ruthenium catalysts are also used as reduction catalysts of a carboxyl group to an alcohol, the decrease in selectivity is obvious (Non Patent Literature 3). It is known that the use of a ruthenium catalyst for hydrogenation of an aromatic carboxylic acid requires conversion of the carboxylic acid to an ester, and such a process involves two additional steps including esterification of the aromatic carboxylic acid and hydrolysis for the alicyclic carboxylic acid (Patent Literature 3 and Patent Literature 4). Similarly, it is known that the use of a ruthenium catalyst for hydrogenation of an aromatic carboxylic acid requires conversion of the carboxylic acid to an inorganic salt such as a sodium salt, and such a process involves two additional steps including derivation of the inorganic salt from the aromatic carboxylic acid, and desalination of the inorganic salt of the alicyclic carboxylic acid.

PRIOR ART DOCUMENTS

Patent Literatures

Patent Literature 1: Japanese Patent Application Publication No. 2008-63263 (JP2008-63263A)
Patent Literature 2: Japanese Patent No. 4622406
Patent Literature 3: Japanese Patent No. 3834836
Patent Literature 4: Japanese Patent Application Publication No. 2006-045166 (JP2006-045166A)

Non Patent Literatures

Non Patent Literature 1: Journal of Organic Chemistry, 1966, Vol. 31, p. 3438 to 3439
Non Patent Literature 2: Chemistry a European Journal, 2009, Vol. 15, p. 6953 to 6963
Non Patent Literature 3: Handbook of Heterogeneous Catalytic Hydrogenation for Organic Synthesis

SUMMARY OF INVENTION

An object of the present invention is to develop a catalyst which uses a relatively inexpensive noble metal, ruthenium, which has an activity equivalent to that of a rhodium catalyst, and which does not undergo the decrease in activity as observed in a rhodium catalyst, and thereby to establish an industrially simple method for producing an alicyclic carboxylic acid.

Because of the above-described catalytic performances of ruthenium, it is difficult to use an inexpensive ruthenium catalyst directly as an alternative to a rhodium catalyst. The present inventors have made intensive study to use ruthenium as a main component. As a result, the present inventors have found the following catalyst which solves the problems of the rhodium catalyst and the problems of the ruthenium catalyst. In this catalyst, palladium is added as a second component, and ruthenium and palladium coexist in the catalyst, and preferably ruthenium and palladium coexist in every single particle on the surface of the support. Based on this finding, the present invention has been developed.

Specifically, the present invention relates to the following methods for producing an alicyclic carboxylic acid of [1] to [9], and the following catalysts of [10] to [13].

[1]

A method for producing an alicyclic carboxylic acid by hydrogenating an aromatic ring of an aromatic carboxylic acid, which comprises using a catalyst containing ruthenium and palladium as a catalyst.

[2]

The method for producing an alicyclic carboxylic acid according to [1], wherein the catalyst is a catalyst in which the ruthenium and the palladium are co-supported on a support.

[3]

The method for producing an alicyclic carboxylic acid according to [1] or [2], wherein one or two or more selected from water, methanol, ethanol, 1-propanol, and 2-propanol are used as a reaction solvent of a hydrogenation reaction.

[4]

The method for producing an alicyclic carboxylic acid according to [1] or [2], wherein water is used as a reaction solvent of a hydrogenation reaction.

[5]

The method for producing an alicyclic carboxylic acid according to [2] to [4], wherein the support of the catalyst comprises one or a combination of two or more selected from activated carbon, alumina, zirconia, ceria, titania, and silica.

[6]
The method for producing an alicyclic carboxylic acid according to [1] to [5], wherein the aromatic carboxylic acid is an aromatic carboxylic acid represented by general formula (1), (2), or (3):

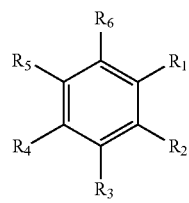
(1)

in formula (1), $R_1$ to $R_6$ are each COOH, $CH_2OH$, $CH_3$, OH, or H, and at least one of $R_1$ to $R_6$ is COOH;

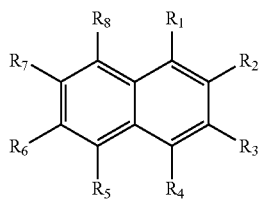
(2)

in formula (2), $R_1$ to $R_8$ are each COOH, $CH_2OH$, $CH_3$, OH, or H, and at least one of $R_1$ to $R_8$ is COOH; and

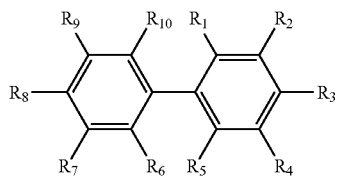
(3)

in formula (3), $R_1$ to $R_{10}$ are each COOH, $CH_2OH$, $CH_3$, OH, or H, and at least one of $R_1$ to $R_{10}$ is COOH.

[7]
The method for producing an alicyclic carboxylic acid according to [1] to [5], wherein the aromatic carboxylic acid is phthalic acid, isophthalic acid, terephthalic acid, trimellitic acid, trimesic acid, or pyromellitic acid.

[8]
The method for producing an alicyclic carboxylic acid according to [1] to [5], wherein the aromatic carboxylic acid is trimellitic acid, trimesic acid, or pyromellitic acid.

[9]
The method for producing an alicyclic carboxylic acid according to [2], wherein the catalyst in which the ruthenium and the palladium are co-supported on the support is a co-supported ruthenium-palladium catalyst in which the ruthenium and the palladium are present in a form of particles containing both the ruthenium and the palladium on a surface of the support.

[10]
A co-supported ruthenium-palladium catalyst, in which ruthenium and palladium are co-supported on a support, wherein the ruthenium and the palladium are present in a form of particles containing both the ruthenium and the palladium on a surface of the support.

[11]
The co-supported ruthenium-palladium catalyst according to [10], wherein the co-supported ruthenium-palladium catalyst is a hydrogenation catalyst.

[12]
The co-supported ruthenium-palladium catalyst according to [10] or [11], wherein the co-supported ruthenium-palladium catalyst is a catalyst for hydrogenating an aromatic ring of an aromatic carboxylic acid.

[13]
The co-supported ruthenium-palladium catalyst according to any one of [10] to [12], wherein the support comprises one or a combination of two or more selected from the group consisting of activated carbon, alumina, zirconia, ceria, titania, and silica.

The catalyst of the present invention exhibits an activity equivalent to that of a rhodium catalyst. In addition, the catalyst of the present invention does not undergo decrease in activity, which is a problem of the rhodium catalyst, and hence does not require activation operation. Accordingly, an alicyclic carboxylic acid can be produced industrially by a very simple process. In addition, the reduction reaction of carboxyl groups, which is observed in the case of a ruthenium catalyst, is inhibited, so that the hydrogenation reaction of the aromatic ring proceeds with a high selectivity.

BRIEF DESCRIPTION OF DRAWINGS

FIG. 5(2) shows an EDX analysis result of a particle observed in the transmission electron microscopic image of the co-supported ruthenium-palladium catalyst produced in Example 21.

FIG. 5(3) shows an EDX analysis result of a particle observed in the transmission electron microscopic image of the co-supported ruthenium-palladium catalyst produced in Example 21.

FIG. 5(4) shows an EDX analysis result of a particle observed in the transmission electron microscopic image of the co-supported ruthenium-palladium catalyst produced in Example 21.

FIG. 5(5) shows an EDX analysis result of a particle observed in the transmission electron microscopic image of the co-supported ruthenium-palladium catalyst produced in Example 21.

FIG. 6(2) shows an EDX analysis result of a particle observed in the transmission electron microscopic image of the co-supported ruthenium-palladium catalyst produced in Example 21.

FIG. 6(3) shows an EDX analysis result of a particle observed in the transmission electron microscopic image of the co-supported ruthenium-palladium catalyst produced in Example 21.

FIG. 6(4) shows an EDX analysis result of a particle observed in the transmission electron microscopic image of the co-supported ruthenium-palladium catalyst produced in Example 21.

FIG. 6(5) shows an EDX analysis result of a particle observed in the transmission electron microscopic image of the co-supported ruthenium-palladium catalyst produced in Example 21.

FIG. 6(6) shows an EDX analysis result of a particle observed in the transmission electron microscopic image of the co-supported ruthenium-palladium catalyst produced in Example 21.

FIG. 7(2) shows an EDX analysis result of a particle observed in the transmission electron microscopic image of the co-supported ruthenium-palladium catalyst produced in Example 22.

FIG. 7(3) shows an EDX analysis result of a particle observed in the transmission electron microscopic image of the co-supported ruthenium-palladium catalyst produced in Example 22.

FIG. 7(4) shows an EDX analysis result of a particle observed in the transmission electron microscopic image of the co-supported ruthenium-palladium catalyst produced in Example 22.

FIG. 7(5) shows an EDX analysis result of a particle observed in the transmission electron microscopic image of the co-supported ruthenium-palladium catalyst produced in Example 22.

FIG. 7(6) shows an EDX analysis result of a particle observed in the transmission electron microscopic image of the co-supported ruthenium-palladium catalyst produced in Example 22.

FIG. 7(7) shows an EDX analysis result of a particle observed in the transmission electron microscopic image of the co-supported ruthenium-palladium catalyst produced in Example 22.

FIG. 8(2) shows an EDX analysis result of a particle observed in the transmission electron microscopic image of the co-supported ruthenium-palladium catalyst produced in Example 22.

FIG. 8(3) shows an EDX analysis result of a particle observed in the transmission electron microscopic image of the co-supported ruthenium-palladium catalyst produced in Example 22.

FIG. 8(4) shows an EDX analysis result of a particle observed in the transmission electron microscopic image of the co-supported ruthenium-palladium catalyst produced in Example 22.

FIG. 8(5) shows an EDX analysis result of a particle observed in the transmission electron microscopic image of the co-supported ruthenium-palladium catalyst produced in Example 22.

FIG. 8(6) shows an EDX analysis result of a particle observed in the transmission electron microscopic image of the co-supported ruthenium-palladium catalyst produced in Example 22.

FIG. 8(7) shows an EDX analysis result of a particle observed in the transmission electron microscopic image of the co-supported ruthenium-palladium catalyst produced in Example 22.

FIG. 8(8) shows an EDX analysis result of a particle observed in the transmission electron microscopic image of the co-supported ruthenium-palladium catalyst produced in Example 22.

DESCRIPTION OF EMBODIMENTS

Figure 1:
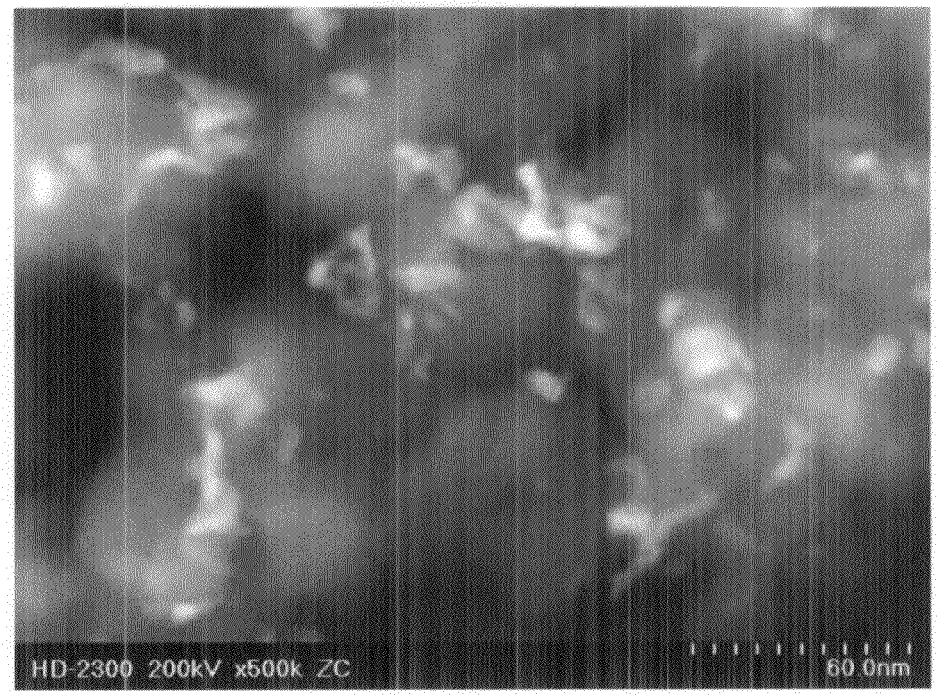
FIG. 1 shows a transmission electron microscopic image (Z-contrast, magnification: ×500 k) of a co-supported ruthenium-palladium catalyst produced in Example 21.

An aromatic carboxylic acid used for this reaction is not particularly limited, as long as the aromatic carboxylic acid is a compound having a carboxyl group on an aromatic ring, and known aromatic carboxylic acids can be used. As the aromatic carboxylic acid, those represented by the above-described general formula (1), (2), or (3) can be used.

Specific examples of the aromatic carboxylic acid include aromatic monocarboxylic acids such as benzoic acid; aromatic dicarboxylic acids such as phthalic acid, isophthalic acid, terephthalic acid, 1,2-naphthalenedicarboxylic acid, 1,4-naphthalenedicarboxylic acid, 1,8-naphthalenedicarboxylic acid, 2,3-naphthalenedicarboxylic acid, 2,6-naphthalenedicarboxylic acid, 1,5-naphthalenedicarboxylic acid, 2,7-naphthalenedicarboxylic acid, 2,2'-biphenyldicarboxylic acid, 3,3'-biphenyldicarboxylic acid, and 4,4'-biphenyldicarboxylic acid; aromatic tricarboxylic acids such as hemimellitic acid, trimellitic acid, trimesic acid, 1,2,4-naphthalenetricarboxylic acid, and 2,5,7-naphthalenetricarboxylic acid; aromatic tetracarboxylic acids such as mellophanic acid, prehnitic acid, pyromellitic acid, 3,3'4,4'-biphenyltetracarboxylic acid, 1,4,5,8-naphthalenetetracarboxylic acid, and 2,3,6,7-naphthalenetetracarboxylic acid; aromatic pentacarboxylic acids such as benzenepentacarboxylic acid; aromatic hexacarboxylic acids such as benzenehexacarboxylic acid; and the like. One of these aromatic carboxylic acids can be used alone, or two or more thereof can be used in combination, as appropriate.

In particular, aromatic dicarboxylic acids, aromatic tricarboxylic acids, and aromatic tetracarboxylic acids each having 2 to 4 carboxyl groups on a benzene ring (s) are preferable. Specific examples thereof include phthalic acid, isophthalic acid, terephthalic acid, trimellitic acid, trimesic acid, and pyromellitic acid. Trimellitic acid, trimesic acid, and pyromellitic acid are further preferable. One of these aromatic carboxylic acids can be used alone, or two or more thereof can be used in combination, as appropriate.

A reaction solvent is preferably used for the hydrogenation reaction of the present invention. The reaction solvent is not particularly limited, as long as the reaction solvent dissolves the aromatic carboxylic acid, and does not inhibit the reaction.

Specific examples the reaction solvent include water; alcohols such as methanol, ethanol, 1-propanol, 2-propanol, 1-butanol, 2-butanol, and 2-methyl-1-propanol; ethers such as diethyl ether, diisopropyl ether, n-butyl ether, cyclopentyl methyl ether, tert-butyl methyl ether, and THF; esters such as methyl acetate and ethyl acetate; and ketones such as acetone and methyl ethyl ketone. Of these reaction solvents, water, methanol, ethanol, 1-propanol, and 2-propanol are preferable, and water is further preferable. One of these reaction solvents can be used alone, or two or more thereof can be used as a mixture, as appropriate.

In the hydrogenation reaction, the aromatic carboxylic acid may be dissolved or suspended in the solvent, and the concentration of the aromatic carboxylic acid is not particularly limited. A specific concentration of the aromatic carboxylic acid is preferably 1 to 50% by weight, more preferably 2 to 40% by weight, and further preferably 2 to 20% by weight, in terms of the aromatic carboxylic acid relative to the total of the aromatic carboxylic acid and the solvent.

The catalyst containing ruthenium and palladium used for the hydrogenation reaction is not limited, as long as ruthenium and palladium coexist in the catalyst. Specific examples thereof include catalysts obtained by mixing a supported ruthenium catalyst and a supported palladium catalyst, and catalysts in which ruthenium and palladium are co-supported on a support. Catalysts in which ruthenium and palladium are co-supported on a support are preferable.

In the present invention, it is preferable to use a co-supported ruthenium-palladium catalyst in which ruthenium and palladium are present in a form of particles containing both ruthenium and palladium on a surface of a support, i.e., in which ruthenium and palladium coexist in every single particle. Since ruthenium and palladium coexist in every single particle, and are close to each other, the catalyst exhibits a high activity and a high selectivity in hydrogenation of an aromatic ring of an aromatic carboxylic acid.

The size of the particles in which ruthenium and palladium coexist and which are present on the surface of the support of the co-supported ruthenium-palladium catalyst is not particularly limited, as long as ruthenium and palladium coexist. It is generally known that a larger size of particles of a supported metal results in a smaller outer surface area of the particles, and hence the supported metal is not efficiently used in the reaction. Also in the case of the co-supported ruthenium-palladium catalyst of the present invention, when the size of the particles in which ruthenium and palladium coexist is large, the outer surface area of the particles becomes small, and the supported ruthenium and palladium are not efficiently used in the reaction. In order to efficiently use the ruthenium and palladium in the hydrogenation reaction, a smaller particle diameter is preferable. The particle diameter is preferably 1 to 50 nm, and more preferably 1 to 15 nm. The particle diameter can be easily measured by transmission electron microscopy or other methods. In addition, the particles are preferably constituted of ruthenium and palladium.

A method for producing the catalyst containing ruthenium and palladium used for the hydrogenation reaction is not limited, as long as ruthenium and palladium can be caused to coexist in the catalyst, and preferably as long as ruthenium and palladium are caused to coexist in every single particle on the surface of the support. It is also possible to add a third component, in addition to ruthenium and palladium. Specific examples of the preparation method include the ion exchange method, the impregnation method, the deposition method, and the like. The impregnation method and the deposition method are preferable.

When ruthenium and palladium are co-supported, the order of supporting ruthenium and palladium on the support is not particularly limited. Specific examples thereof include a simultaneous supporting method, a sequential supporting method, and the like.

After ruthenium and palladium are incorporated into the catalyst, it is also possible to perform drying, calcination, and reduction, as appropriate, depending on the preparation method.

The amounts of ruthenium and palladium contained in the catalyst are not limited. It is only necessary that a larger amount of the catalyst be used for the hydrogenation reaction when the contents of ruthenium and palladium are low, while a smaller amount of the catalyst be used for the hydrogenation reaction when the contents of ruthenium and palladium are high. Specifically, the total content of ruthenium and palladium is preferably 0.5 to 10% by weight, and more preferably 0.5 to 5% by weight. The total amount of ruthenium and palladium supported can be determined by X-ray fluorescence analysis or the like.

The ratios of ruthenium and palladium among metals contained in the catalyst are not limited, as long as ruthenium and palladium coexist in the catalyst. A specific ratio of each of ruthenium and palladium is preferably 1 to 99% by weight, more preferably 10 to 90% by weight, and further preferably 20 to 80% by weight.

The support of the catalyst is not particularly limited, as long as ruthenium and palladium can be supported on the support. The shape of the support (for example, powder, molded article, or the like) and physical properties of the support (for example, specific surface area, average pore diameter, and the like) are not limited, either. Specific examples of the support include activated carbon, alumina, zirconia, ceria, titania, silica, silica-alumina, zeolite, chromium oxide, tungsten oxide, ion-exchange resins, synthetic adsorbents, and the like. Of these supports, activated carbon, alumina, zirconia, ceria, titania, and silica are preferable. One of these supports can be used alone, or two or more thereof can be used as a mixture, as appropriate. In addition, the particle diameter (average particle diameter) of the support is preferably 1 μm to 300 μm in a case of a slurry bed reaction, and preferably 0.3 mm to 10 mm in a case of a fixed bed reaction.

The amount of the catalyst used for the hydrogenation reaction is not limited, and may be determined, as appropriate, in consideration of the contents of ruthenium and palladium and the amount of the aromatic carboxylic acid used for the reaction, so that a desired reaction time can be achieved.

The temperature of the hydrogenation reaction is not limited. Too low a temperature results in a low reaction rate, so that a longer time is required for the completion of the hydrogenation reaction. On the other hand, too high a temperature results in a high reaction rate, so that a shorter time is required for the completion of the hydrogenation reaction, but the selectivity to the desired alicyclic carboxylic acid is lowered. The reaction can be carried out in a temperature range from 40 to 150° C., and preferably in a temperature range from 40 to 100° C.

The hydrogen pressure in the hydrogenation reaction is not particularly limited. A low hydrogen pressure results in a low reaction rate, so that a longer time is required for the completion of the hydrogenation reaction. On the other hand, a high hydrogen pressure leads to increase in the investment in apparatus such as that for obtaining an apparatus with pressure resistant specifications, and the like, although a shorter time is required for the completion of the hydrogenation reaction. Specifically, the hydrogenation reaction can be carried out at a hydrogen pressure in a range from 1 to 15 MPa, and the hydrogen pressure is preferably 5 to 10 MPa.

The reaction mode, such as a batch mode or a continuous mode, of the hydrogenation reaction is not limited. When the desired production amount is small, a production process of a batch mode may be created. When the production amount is large, a production process of a continuous mode may be created.

In a batch mode, the catalyst containing ruthenium and palladium used for the hydrogenation reaction can be reused without performing any activation operation on the catalyst, because the activity of the catalyst is not significantly lowered in each reaction. In a continuous mode, the activity is not significantly lowered, even when a continuous operation is performed for 1000 hours or more (5000 hours or more in a case of a co-supported ruthenium-palladium catalyst in which ruthenium and palladium are present in a form of particles containing both ruthenium and palladium on the surface of the support).

By implementation of the present invention as described above, it is possible to produce an alicyclic carboxylic acid in a simple and easy process and by an industrially advantageous method.

Note that, by combining, as appropriate, the amount of the aromatic carboxylic acid, the amount of the catalyst, the reaction temperature, the hydrogen pressure, and the reaction mode, which are described above, the hydrogenation reaction of the present invention using, as a catalyst, the co-supported ruthenium-palladium catalyst in which ruthenium and palladium are present in a form of particles containing both ruthenium and palladium on the surface of the support makes it possible to produce an alicyclic carboxylic acid with a desired selectivity in a desired reaction time.

EXAMPLES

Next, the present invention will be described in further detail based on Examples. However, the present invention is not limited to these Examples at all.

Note that the conversion of each aromatic carboxylic acid and the selectivity to each alicyclic carboxylic acid were determined by converting the reaction product to a methyl ester derivative, and then analyzing the derivative by gas chromatography.

Example 1

Into a 30-ml SUS-316 autoclave, 1.0 g of trimellitic acid (manufactured by Tokyo Chemical Industry Co., Ltd.), 0.5 g of a 1.0% by weight Ru-4.0% by weight Pd/carbon powder catalyst prepared by a known method (the deposition method described on Page 40 of Handbook of Heterogeneous Catalytic Hydrogenation for Organic Synthesis), and 10 g of water were introduced. The pressure was raised to 10 MPa with hydrogen, and the temperature was raised to 60° C., with stirring using a stirrer chip. Absorption of hydrogen stopped in 0.5 hours from the start of the temperature raise, which indicated the completion of the reaction. The reaction product was converted to a methyl ester derivative, and then analyzed by gas chromatography. The conversion of trimellitic acid was 100%, and the selectivity to hydrogenated trimellitic acid (1,2,4-cyclohexanetricarboxylic acid) was 98.6% (% by mole).

Example 2

Into a 30-ml SUS-316 autoclave, 1.0 g of trimellitic acid (manufactured by Tokyo Chemical Industry Co., Ltd.), 0.5 g of a 2.5% by weight Ru-2.5% by weight Pd/carbon powder catalyst prepared by the same method as described in Example 1, and 10 g of water were introduced. The pressure was raised to 10 MPa with hydrogen, and the temperature was raised to 60° C., with stirring using a stirrer chip. Absorption of hydrogen stopped in 0.5 hours from the start of the temperature raise, which indicated the completion of the reaction. The reaction product was converted to a methyl ester derivative, and then analyzed by gas chromatography. The conversion of trimellitic acid was 100%, and the selectivity to hydrogenated trimellitic acid was 96.9% (% by mole).

Example 3

Into a 30-ml SUS-316 autoclave, 1.0 g of trimellitic acid (manufactured by Tokyo Chemical Industry Co., Ltd.), 0.5 g of a 4.0% by weight Ru-1.0% by weight Pd/carbon powder catalyst prepared by the same method as described in Example 1, and 10 g of water were introduced. The pressure was raised to 10 MPa with hydrogen, and the temperature was raised to 60° C., with stirring using a stirrer chip. Absorption of hydrogen stopped in 0.6 hours from the start of the temperature raise, which indicated the completion of the reaction. The reaction product was converted to a methyl ester derivative, and then analyzed by gas chromatography. The conversion of trimellitic acid was 100%, and the selectivity to hydrogenated trimellitic acid was 97.2% (% by mole).

Example 4

Into a 300-ml SUS-316 autoclave, 20 g of trimellitic acid (manufactured by Tokyo Chemical Industry Co., Ltd.), 2 g of a 4.0% by weight Ru-1.0% by weight Pd/carbon powder catalyst prepared by the same method as described in Example 1, and 120 g of water were introduced. The pressure was raised to 10 MPa with hydrogen, and the temperature was raised to 60° C., with stirring using a magnetic stirring impeller. Absorption of hydrogen stopped in 1.2 hours from the start of the temperature raise, which indicated the completion of the reaction. The reaction product was converted to a methyl ester derivative, and then analyzed by gas chromatography. The conversion of trimellitic acid was 100%, and the selectivity to hydrogenated trimellitic acid was 94.2% (% by mole).

Example 5

Into a 30-ml SUS-316 autoclave, 1.5 g of trimellitic acid (manufactured by Tokyo Chemical Industry Co., Ltd.), 0.3 g of a 2.5% by weight Ru-2.5% by weight Pd/carbon powder catalyst prepared by the same method as described in Example 1, and 9 g of water were introduced. The pressure was raised to 10 MPa with hydrogen, and the temperature was raised to 60° C., with stirring using a stirrer chip. Absorption of hydrogen stopped in 1.8 hours from the start of the temperature raise, which indicated the completion of the reaction. The reaction product was converted to a methyl ester derivative, and then analyzed by gas chromatography. The conversion of trimellitic acid was 100%, and the selectivity to hydrogenated trimellitic acid was 95.1% (% by mole).

Example 6

Into a 30-ml SUS-316 autoclave, 1.5 g of trimellitic acid (manufactured by Tokyo Chemical Industry Co., Ltd.), 0.3 g of a 2.5% by weight Ru-2.5% by weight Pd/alumina powder catalyst prepared by the same method as described in Example 1, and 9 g of water were introduced. The pressure was raised to 10 MPa with hydrogen, and the temperature was raised to 60° C., with stirring using a stirrer chip. Absorption of hydrogen stopped in 1.7 hours from the start of the temperature raise, which indicated the completion of the reaction. The reaction product was converted to a methyl ester derivative, and then analyzed by gas chromatography. The conversion of trimellitic acid was 100%, and the selectivity to hydrogenated trimellitic acid was 94.2% (% by mole).

Example 7

Into a 30-ml SUS-316 autoclave, 1.5 g of trimellitic acid (manufactured by Tokyo Chemical Industry Co., Ltd.), 0.3 g of a 2.5% by weight Ru-2.5% by weight Pd/zirconia powder catalyst prepared by the same method as described in Example 1, and 9 g of water were introduced. The pressure was raised to 10 MPa with hydrogen, and the temperature was raised to 60° C., with stirring using a stirrer chip. Absorption of hydrogen stopped in 2.0 hours from the start of the temperature raise, which indicated the completion of the reaction. The reaction product was converted to a methyl ester derivative, and then analyzed by gas chromatography. The conversion of trimellitic acid was 100%, and the selectivity to hydrogenated trimellitic acid was 93.3% (% by mole).

Example 8

Into a 30-ml SUS-316 autoclave, 1.5 g of trimellitic acid (manufactured by Tokyo Chemical Industry Co., Ltd.), 0.3 g of a 2.5% by weight Ru-2.5% by weight Pd/ceria powder catalyst prepared by the same method as described in Example 1, and 9 g of water were introduced. The pressure was raised to 10 MPa with hydrogen, and the temperature was raised to 60° C., with stirring using a stirrer chip. Absorption of hydrogen stopped in 1.6 hours from the start of the temperature raise, which indicated the completion of the reaction. The reaction product was converted to a methyl ester derivative, and then analyzed by gas chromatography. The conversion of trimellitic acid was 100%, and the selectivity to hydrogenated trimellitic acid was 92.7% (% by mole).

Example 9

Into a 200-ml SUS-316 autoclave, 6 g of trimellitic acid (manufactured by Tokyo Chemical Industry Co., Ltd.), 1.2 g of a 2.5% by weight Ru-2.5% by weight Pd/titania powder catalyst prepared by the same method as described in Example 1, and 36 g of water were introduced. The pressure was raised to 9 MPa with hydrogen, and the temperature was raised to 55° C., with stirring using a magnetic stirring impeller. Absorption of hydrogen stopped in 1.5 hours from the start of the temperature raise, which indicated the completion of the reaction. The reaction product was converted to a methyl ester derivative, and then analyzed by gas chromatography. The conversion of trimellitic acid was 100%, and the selectivity to hydrogenated trimellitic acid was 94.0% (% by mole).

Example 10

Into a 200-ml SUS-316 autoclave, 6 g of trimellitic acid (manufactured by Tokyo Chemical Industry Co., Ltd.), 1.2 g of a 2.5% by weight Ru-2.5% by weight Pd/silica powder catalyst prepared by a known method (the impregnation method described on Page 49 of SHOKUBAI CHOUSEI KAGAKU (Catalyst preparation chemistry)), and 36 g of water were introduced. The pressure was raised to 9 MPa with hydrogen, and the temperature was raised to 50° C., with stirring using a magnetic stirring impeller. Absorption of hydrogen stopped in 2.0 hours from the start of the temperature raise, which indicated the completion of the reaction. The reaction product was converted to a methyl ester derivative, and then analyzed by gas chromatography. The conversion of trimellitic acid was 100%, and the selectivity to hydrogenated trimellitic acid was 94.1% (% by mole).

Example 11

Into a 300-ml SUS-316 autoclave, 20 g of trimellitic acid (manufactured by Tokyo Chemical Industry Co., Ltd.), 4.0 g of a 1.0% by weight Ru-1.0% by weight Pd/titania powder catalyst prepared by the same method as described in Example 1, and 120 g of water were introduced. The pressure was raised to 8 MPa with hydrogen, and the temperature was raised to 60° C., with stirring using a magnetic stirring impeller. Absorption of hydrogen stopped in 2.0 hours after the temperature raise to 60° C., which indicated the completion of the reaction. The reaction product was converted to a methyl ester derivative, and then analyzed by gas chromatography. The conversion of trimellitic acid was 100%, and the selectivity to hydrogenated trimellitic acid was 93.5%.

The reaction was repeated under the same conditions, without activating the recovered catalyst. Up to the 7th reaction, the conversion of trimellitic acid was 100%, and the average selectivity to hydrogenated trimellitic acid was 93.6% (% by mole).

Example 12

Into a 200-ml SUS-316 autoclave, 6 g of trimellitic acid (manufactured by Tokyo Chemical Industry Co., Ltd.), 3.0 g of a 1.0% by weight Ru-1.0% by weight Pd/titania powder catalyst prepared by the same method as described in Example 1, and 36 g of water were introduced. The pressure was raised to 9 MPa with hydrogen, and the temperature was raised to 50° C., with stirring using a magnetic stirring impeller. Absorption of hydrogen stopped in 1.3 hours from the start of the temperature raise, which indicated the completion of the reaction. The reaction product was converted to a methyl ester derivative, and then analyzed by gas chromatography. The conversion of trimellitic acid was 100%, and the selectivity to hydrogenated trimellitic acid was 94.4% (% by mole).

Example 13

Into a SUS-316 reaction tube having an inner diameter of 17 mm and a length of 320 mm, 10 g (25 ml) of a 1.0% by weight Ru-1.0% by weight Pd/spherical silica catalyst prepared by the same method as described in Example 10 was packed. A reaction was allowed to proceed bypassing an aqueous solution of 2% by weight trimellitic acid (manufactured by Tokyo Chemical Industry Co., Ltd.) at 30 g/hr and hydrogen at 1.8 L/hr under conditions of a temperature of 80° C. and a hydrogen pressure of 8 MPa. No decrease in conversion of trimellitic acid was observed at 1400 hours from the start of the reaction, and the conversion was maintained at 89% from the initial stage of the reaction. During this period, the selectivity to hydrogenated trimellitic acid stayed around 94% (% by mole).

Example 14

Into a 200-ml SUS-316 autoclave, 6 g of pyromellitic acid (manufactured by Tokyo Chemical Industry Co., Ltd.), 1.2 g of a 2.5% by weight Ru-2.5% by weight Pd/titania powder catalyst prepared by the same method as described in Example 1, and 36 g of water were introduced. The pressure was raised to 9 MPa with hydrogen, and the temperature was raised to 50° C., with stirring using a magnetic stirring impeller. Absorption of hydrogen stopped in 3.0 hours from the start of the temperature raise, which indicated the completion of the reaction. The reaction product was converted to a methyl ester derivative, and then analyzed by gas chromatography. The conversion of pyromellitic acid was 100%, and the selectivity to hydrogenated pyromellitic acid (1,2,4,5-cyclohexanetetracarboxylic acid) was 94.5% (% by mole).

Example 15

Into a 30-ml SUS-316 autoclave, 1.5 g of trimesic acid (manufactured by Tokyo Chemical Industry Co., Ltd.), 0.3 g of a 2.5% by weight Ru-2.5% by weight Pd/titania powder catalyst prepared by the same method as described in Example 1, and 9 g of water were introduced. The pressure was raised to 10 MPa with hydrogen, and the temperature was raised to 60° C., with stirring using a stirrer chip. Absorption of hydrogen stopped in 1.4 hours from the start of the temperature raise, which indicated the completion of the reaction. The reaction product was converted to a methyl ester derivative, and then analyzed by gas chromatography. The conversion of trimesic acid was 100%, and the selectivity to hydrogenated trimesic acid (1,3,5-cyclohexanetricarboxylic acid) was 93.0% (% by mole).

Comparative Example 1

Into a 300-ml SUS-316 autoclave, 20 g of trimellitic acid (manufactured by Tokyo Chemical Industry Co., Ltd.), 1.6 g of a 5.0% by weight Ru/carbon powder catalyst prepared by the same method as described in Example 1, and 120 g of water were introduced. The pressure was raised to 10 MPa with hydrogen, and the temperature was raised to 100° C., with stirring using a magnetic stirring impeller. Although the absorption of hydrogen continued even after 8.2 hours had elapsed from the temperature raise to 100° C., the reaction was stopped. The reaction product was converted to a methyl ester derivative, and then analyzed by gas chromatography. The conversion of trimellitic acid was 87.1%, and the selectivity to hydrogenated trimellitic acid was 60.4% (% by mole).

Comparative Example 2

Into a 30-ml SUS-316 autoclave, 1.0 g of trimellitic acid (manufactured by Tokyo Chemical Industry Co., Ltd.), 0.5 g of a 5.0% by weight Pd/carbon powder catalyst prepared by the same method as described in Example 1, and 10 g of water were introduced. The pressure was raised to 10 MPa with hydrogen, and the temperature was raised to 60° C., with stirring using a stirrer chip. Although the absorption of hydrogen continued even after 3 hours had elapsed from the start of the temperature raise, the reaction was stopped. The reaction product was converted to a methyl ester derivative, and then analyzed by gas chromatography. The conversion of trimellitic acid was 77.0%, and the selectivity to hydrogenated trimellitic acid was 96.3% (% by mole).

Comparative Example 3

Into a 30-ml SUS-316 autoclave, 1.5 g of trimellitic acid (manufactured by Tokyo Chemical Industry Co., Ltd.), 0.3 g of a 5.0% by weight Ru/titania powder catalyst prepared by the same method as described in Example 1, and 9 g of water were introduced. The pressure was raised to 10 MPa with hydrogen, and the temperature was raised to 60° C., with stirring using a stirrer chip. Although the absorption of hydrogen continued even after 3 hours had elapsed from the start of the temperature raise, the reaction was stopped. The reaction product was converted to a methyl ester derivative, and then analyzed by gas chromatography. The conversion of trimellitic acid was 8.6%, and the selectivity to hydrogenated trimellitic acid was 70.5% (% by mole).

Comparative Example 4

Into a 30-ml SUS-316 autoclave, 1.5 g of trimellitic acid (manufactured by Tokyo Chemical Industry Co., Ltd.), 0.3 g of a 5.0% by weight Pd/titania powder catalyst prepared by the same method as described in Example 1, and 9 g of water were introduced. The pressure was raised to 10 MPa with hydrogen, and the temperature was raised to 60° C., with stirring using a stirrer chip. Although the absorption of hydrogen continued even after 3 hours had elapsed from the start of the temperature raise, the reaction was stopped. The reaction product was converted to a methyl ester derivative, and then analyzed by gas chromatography. The conversion of trimellitic acid was 9.2%, and the selectivity to hydrogenated trimellitic acid was 79.3% (% by mole).

Comparative Example 5

Into a 300-ml SUS-316 autoclave, 20 g of trimellitic acid (manufactured by Tokyo Chemical Industry Co., Ltd.), 1.6 g of a 5.0% by weight Rh/carbon powder catalyst manufactured by N.E. CHEMCAT Corporation, and 120 g of water were introduced. The pressure was raised to 8 MPa with hydrogen, and the temperature was raised to 40° C., with stirring using a magnetic stirring impeller. Absorption of hydrogen stopped in 4.0 hours after the temperature raise to 40° C., which indicated the completion of the reaction. The reaction product was converted to a methyl ester derivative, and then analyzed by gas chromatography. The conversion of trimellitic acid was 100%, and the selectivity to hydrogenated trimellitic acid was 97.2% (% by mole).

The reaction was repeated under the same conditions, without activating the recovered catalyst. However, no absorption of hydrogen was observed, and the conversion of trimellitic acid was 0%.

Comparative Example 6

Into a SUS-316 reaction tube having an inner diameter of 17 mm and a length of 320 mm, 10 g (18 ml) of a 2.0% by weight Ru/particulate carbon catalyst prepared by the same method as described in Example 1 was packed. A reaction was allowed to proceed by passing an aqueous solution of 2% by weight trimellitic acid (manufactured by Tokyo Chemical Industry Co., Ltd.) at 30 g/hr and hydrogen at 1.8 L/hr under conditions of a temperature of 60° C. and a hydrogen pressure of 5 MPa. At 20 hours from the start of the reaction, the conversion of trimellitic acid was 22%, and the selectivity to hydrogenated trimellitic acid was 86% (% by mole).

Comparative Example 7

Into a SUS-316 reaction tube having an inner diameter of 17 mm and a length of 320 mm, 10 g (18 ml) of a 2.0% by weight Ru/spherical alumina catalyst prepared by the same method as described in Example 1 was packed. A reaction was allowed to proceed by passing an aqueous solution of 2% by weight trimellitic acid (manufactured by Tokyo Chemical Industry Co., Ltd.) at 30 g/hr and hydrogen at 1.8 L/hr under conditions of a temperature of 60° C. and a hydrogen pressure of 5 MPa. At 6 hours from the start of the reaction, the conversion of trimellitic acid was 23%, and the selectivity to hydrogenated trimellitic acid was 88% (% by mole).

Example 21

In water, 0.647 g of ruthenium chloride n-hydrate (manufactured by Wako Pure Chemical Industries, Ltd.) and 0.417 g of palladium chloride (manufactured by Wako Pure Chemical Industries, Ltd.) were dissolved. To 10 g of silica gel (CARiACT Q50 manufactured by Fuji Silysia Chemical Ltd. and having particle diameters of 75 to 150 μm), the aqueous solution in which ruthenium chloride and palladium chloride were dissolved was added, so that the total weight was adjusted to 60 g. Water was vaporized by heating in a water bath under reduced pressure achieved by using an aspirator. Thus, ruthenium chloride and palladium chloride were supported on the support. After that, drying at 150° C. for 2 hours, calcination in an air atmosphere at 400° C. for 4 hours, and a vapor phase hydrogen reduction at 250° C. for 4 hours were performed. Thus, a co-supported ruthenium-palladium catalyst (2.5% by weight Ru-2.5% by weight Pd/$SiO_2$) was prepared.

Figure 2:
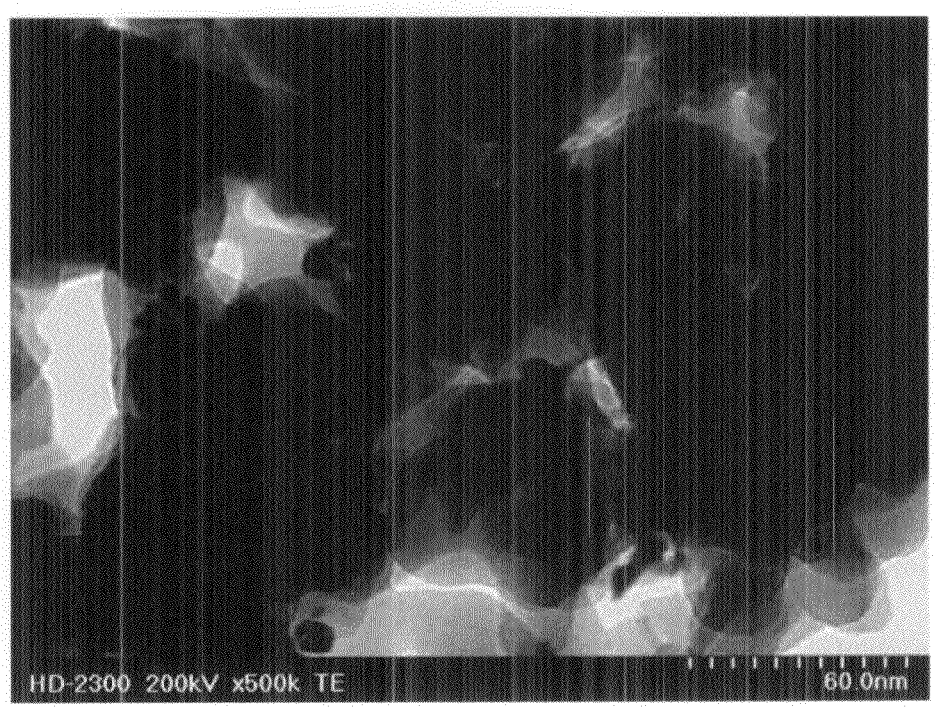
FIG. 2 shows a transmission electron microscopic image (transmission electron image, magnification: ×500 k) of the co-supported ruthenium-palladium catalyst produced in Example 21.
Figure 5:
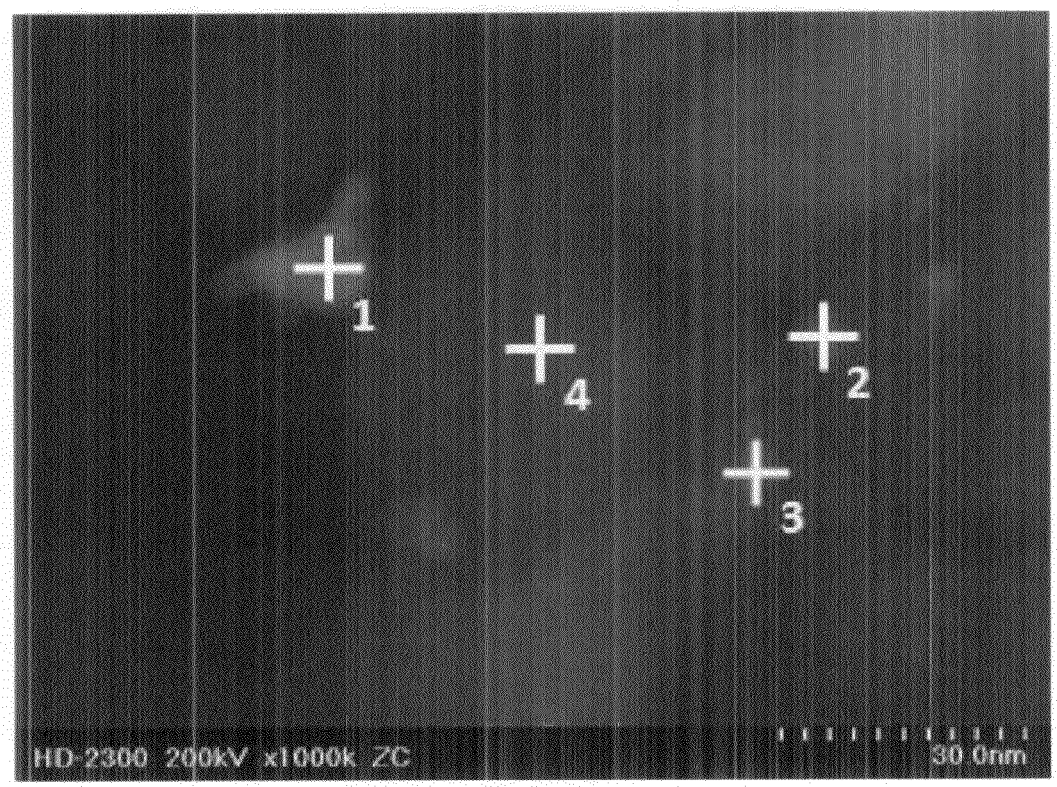
FIG. 5(1) shows an EDX analysis result of particles observed in a transmission electron microscopic image of the co-supported ruthenium-palladium catalyst produced in Example 21.
Figure 5:
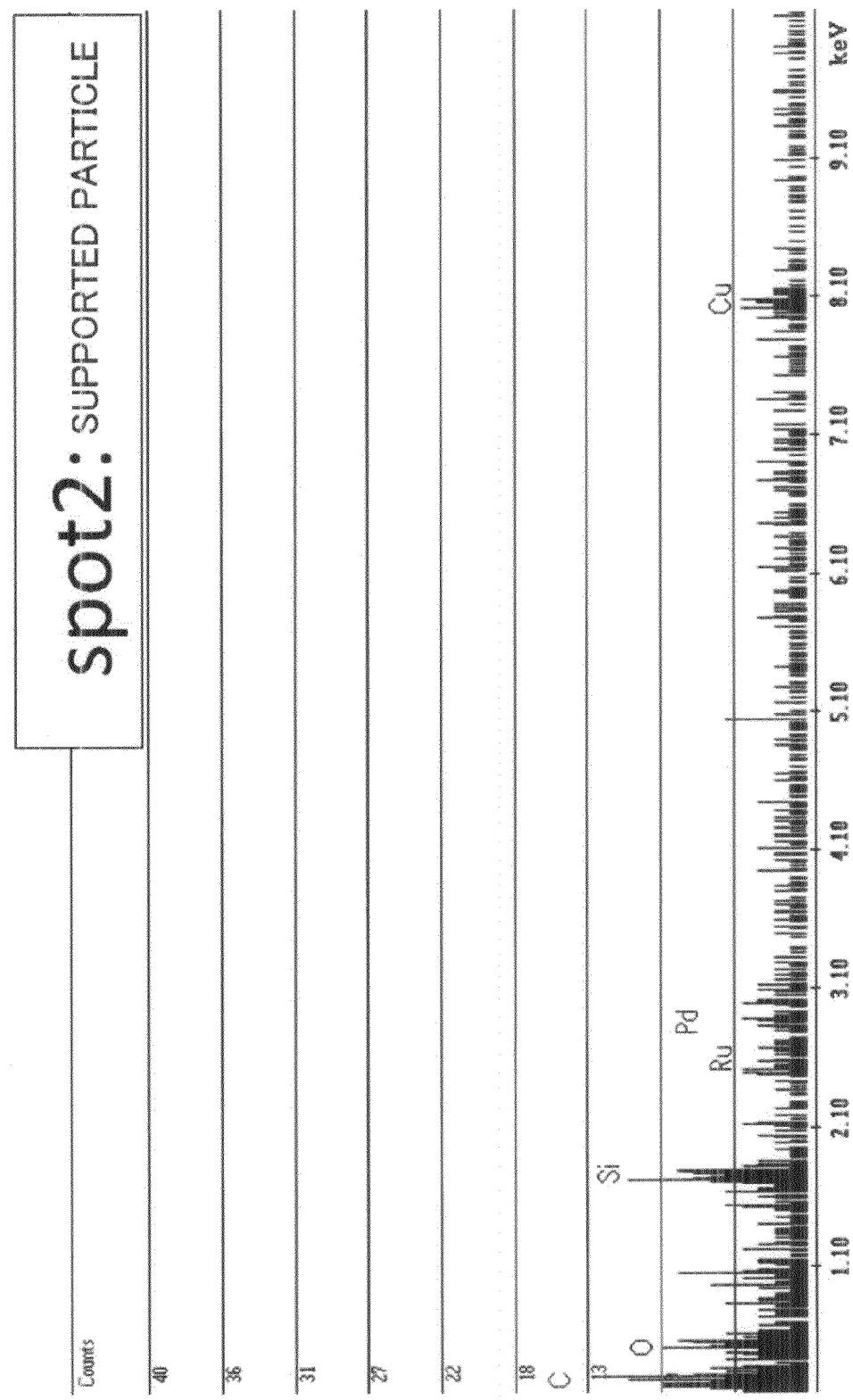
Figure 6:
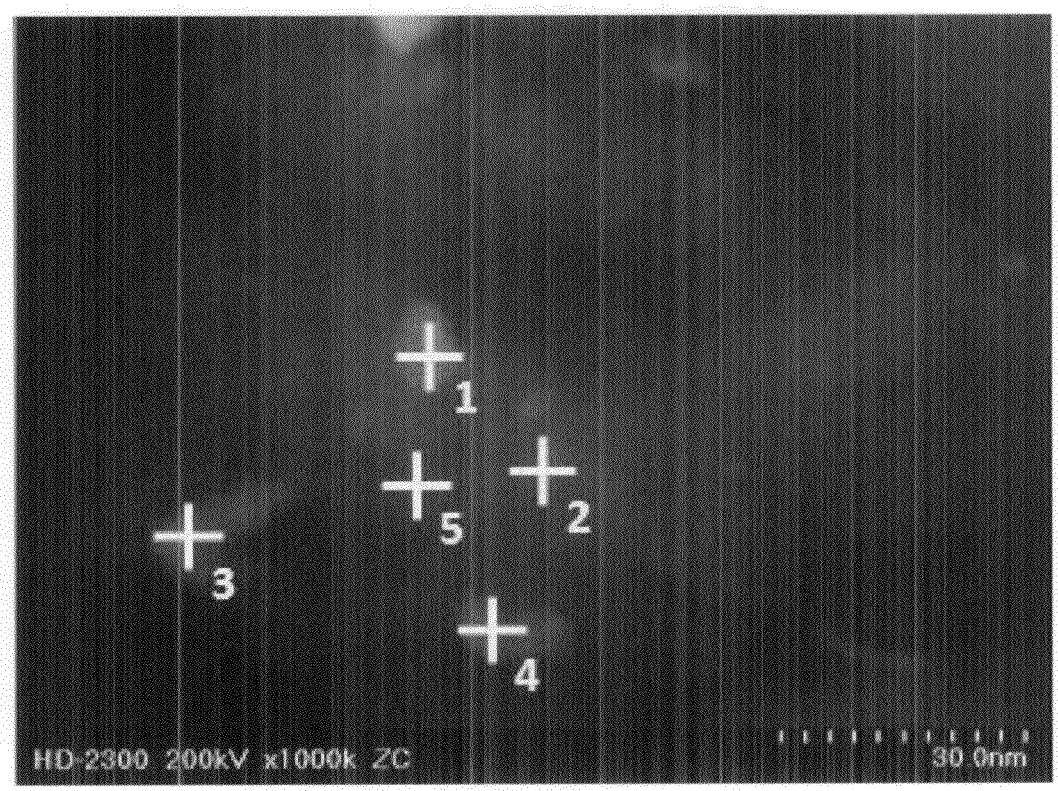
FIG. 6(1) shows EDX analysis results of particles observed in a transmission electron microscopic image of the co-supported ruthenium-palladium catalyst produced in Example 21.
Figure 6:
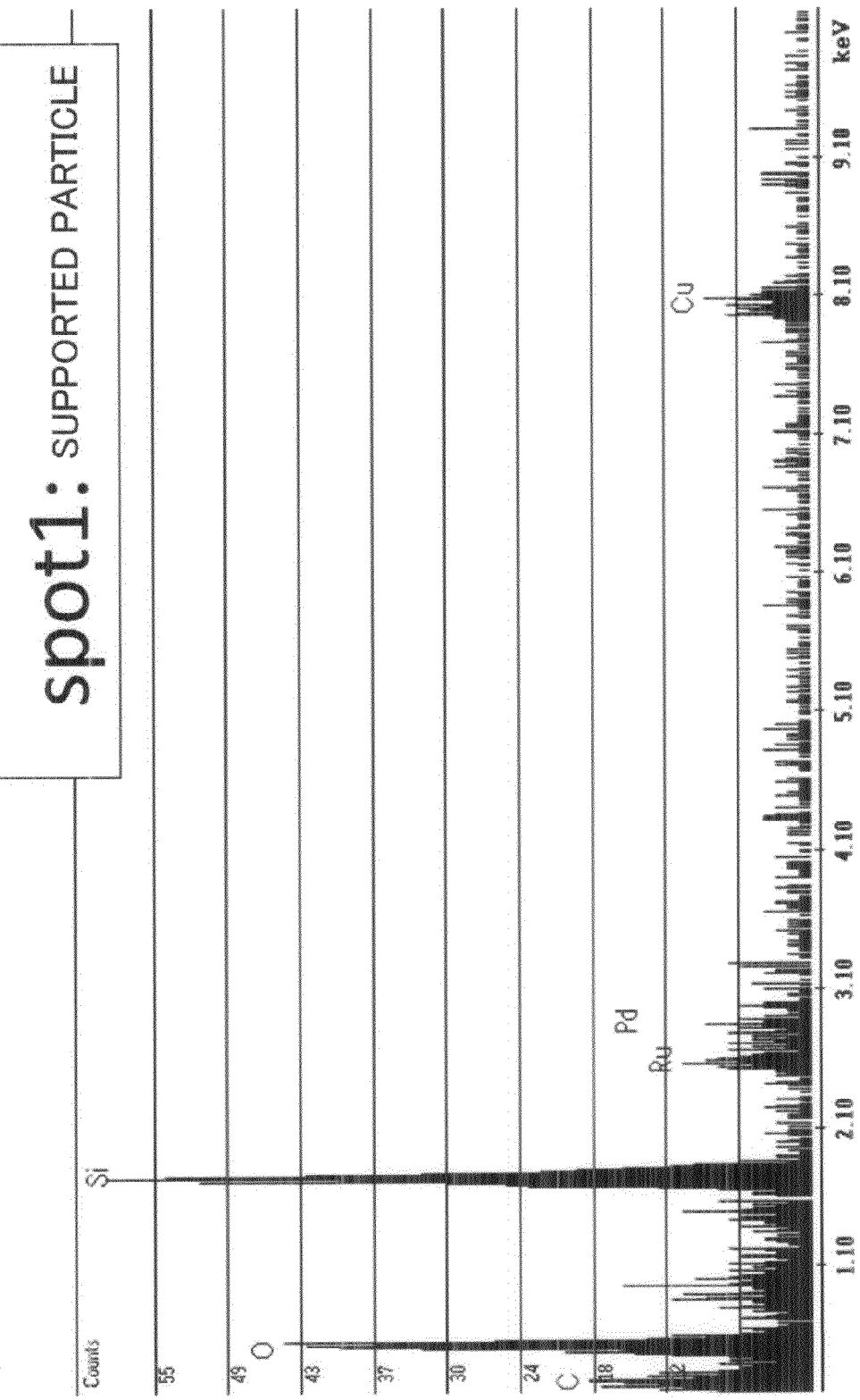
Figure 6:
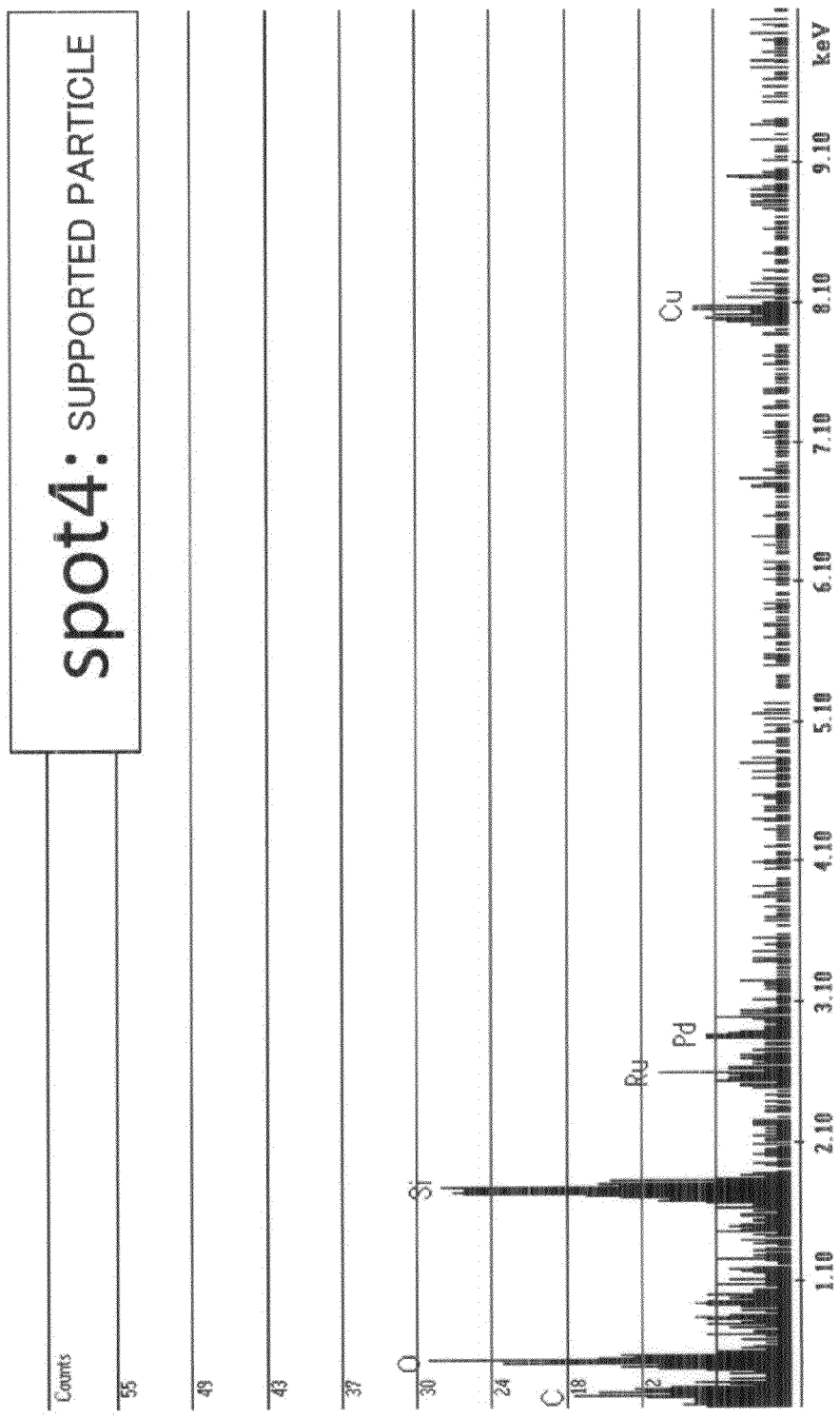
Figure 6:
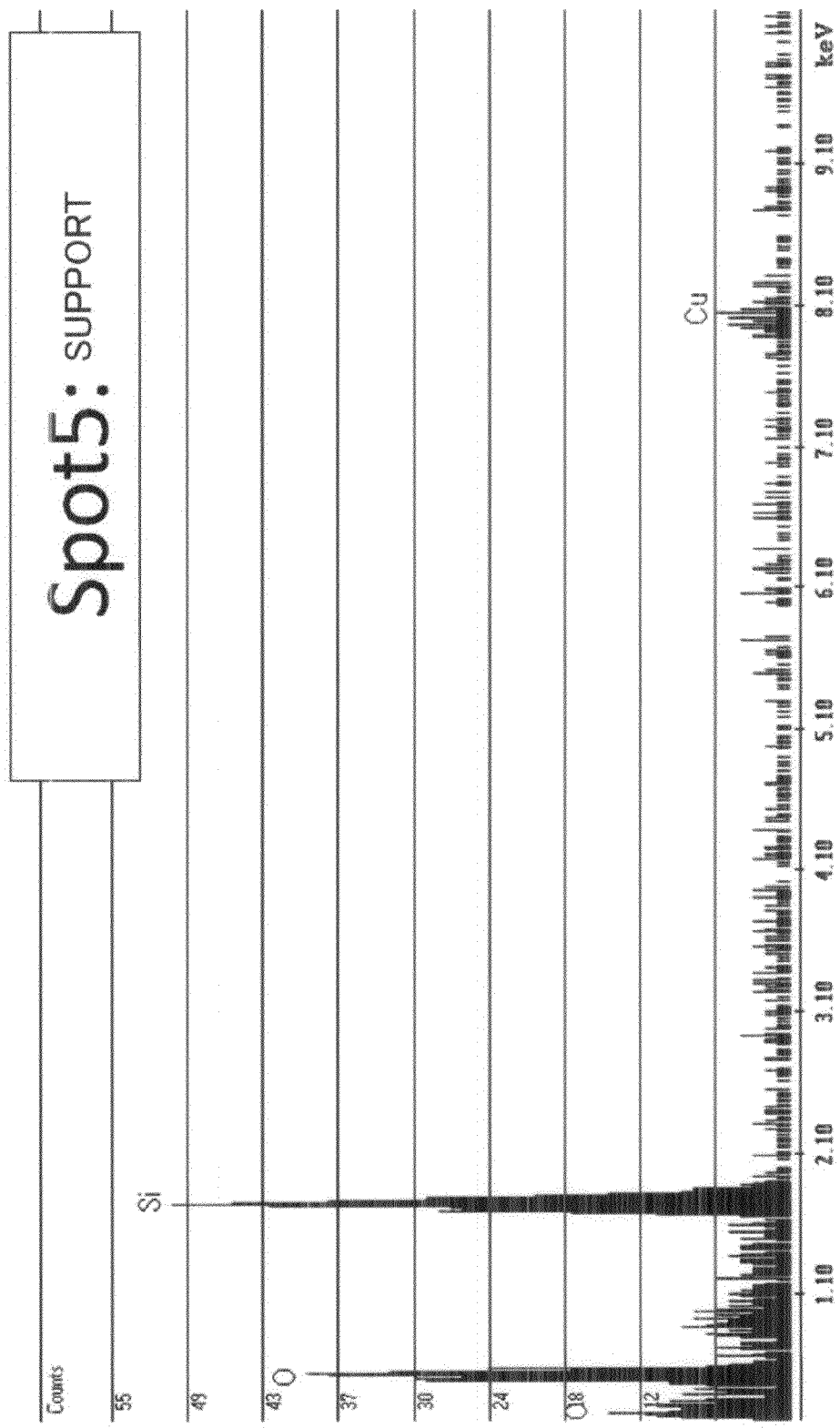

FIGS. 1 and 2 show transmission electron microscopic images of the co-supported ruthenium-palladium catalyst prepared by this method. The sizes of particles present on the surface of the support were 3 to 50 nm. FIGS. 5 and 6 show EDX analysis results of coexistent states of ruthenium and palladium in the particles. The average value of the molar ratios of ruthenium and palladium contained in the particles was 1.

Example 22

A co-supported ruthenium-palladium catalyst (2.5% by weight Ru-2.5% by weight Pd/$SiO_2$) was prepared in the same manner as in Example 21, except that the metal sources were changed to ruthenium acetylacetonate complex (manufactured by Aldrich) and palladium acetate (manufactured by Kojima Chemicals Co., Ltd.), and the solvent was changed to acetonitrile.

Figure 3:
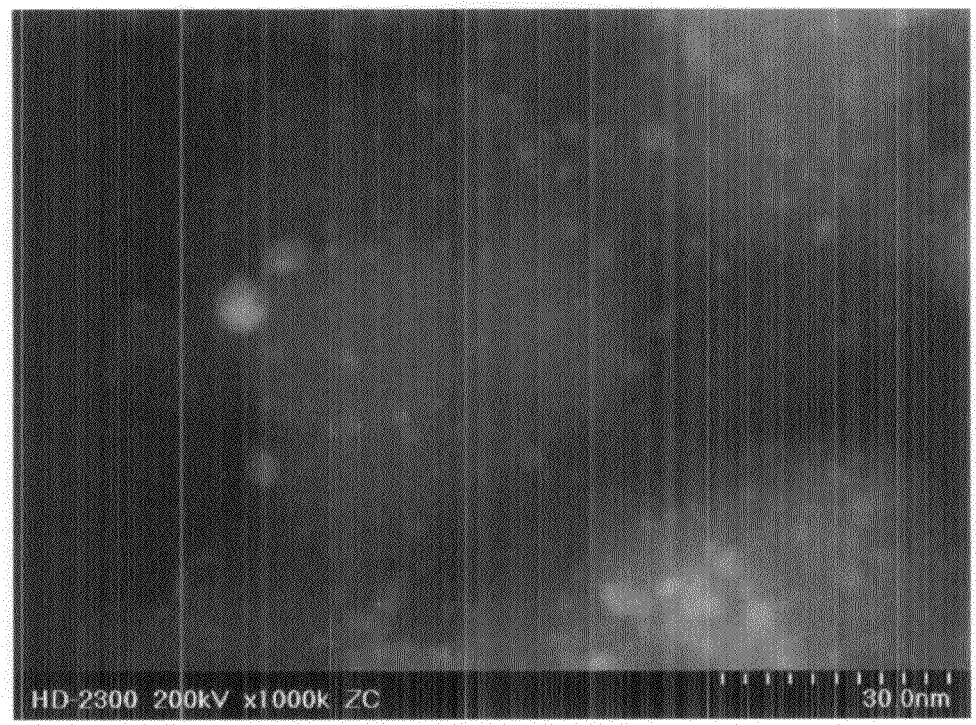
FIG. 3 shows a transmission electron microscopic image (Z-contrast, magnification: ×1,000 k) of a co-supported ruthenium-palladium catalyst produced in Example 22.
Figure 4:
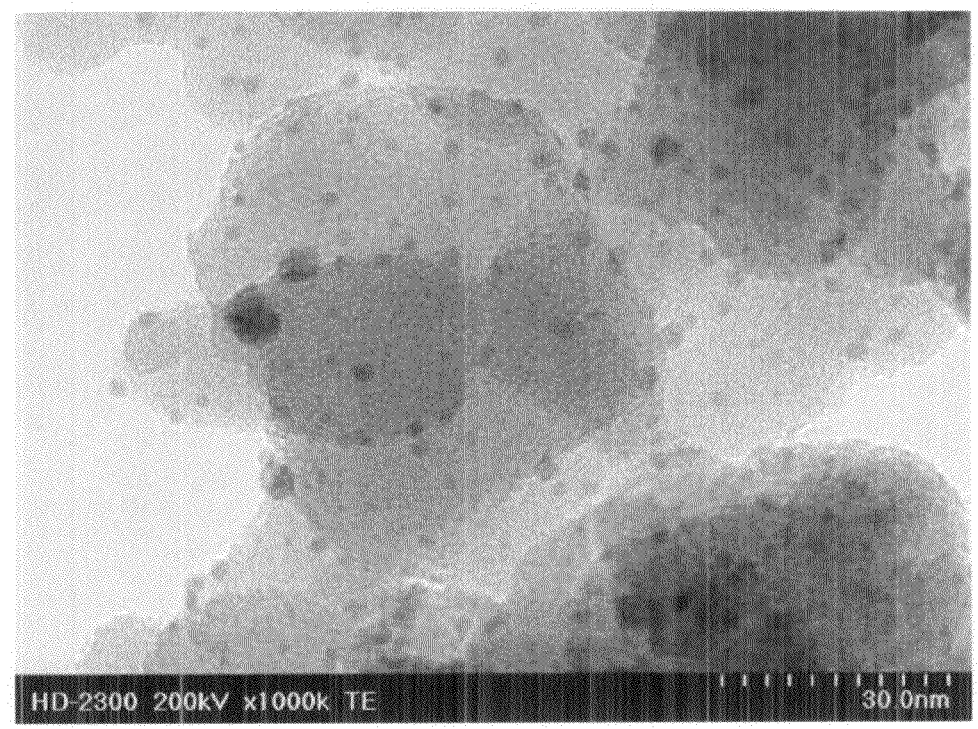
FIG. 4 shows a transmission electron microscopic image (transmission electron image, magnification: ×1,000 k) of the co-supported ruthenium-palladium catalyst produced in Example 22.
Figure 7:
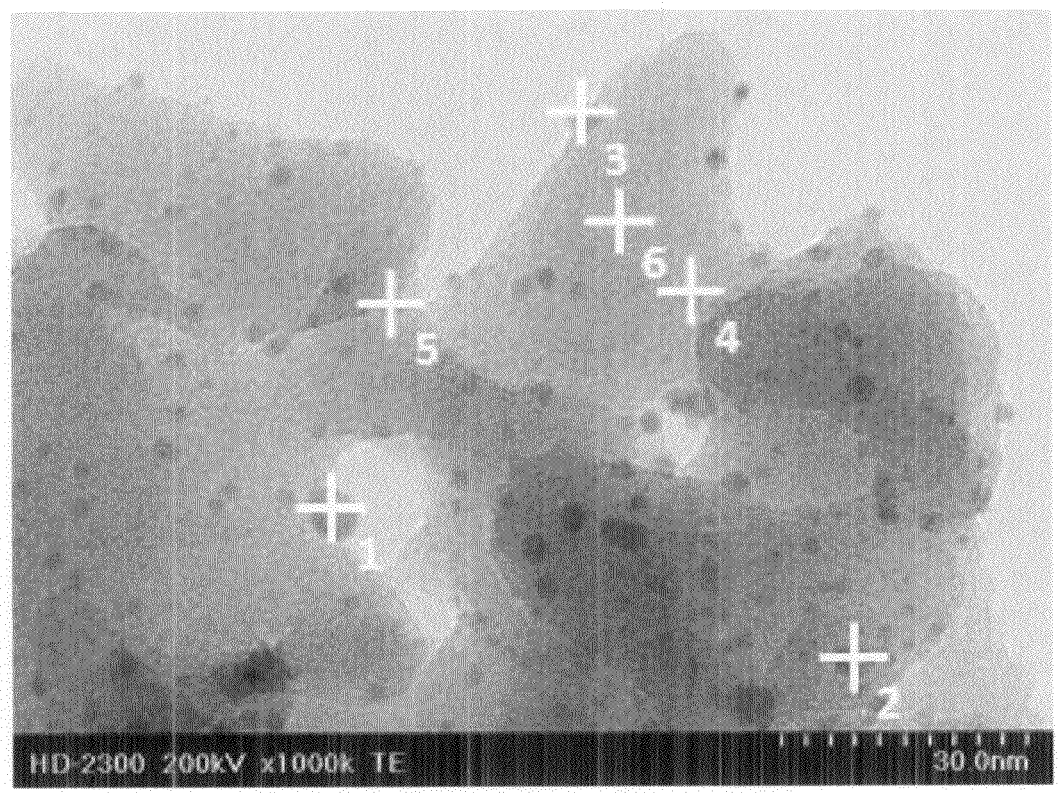
FIG. 7(1) shows EDX analysis results of particles observed in a transmission electron microscopic image of the co-supported ruthenium-palladium catalyst produced in Example 22.
Figure 7:
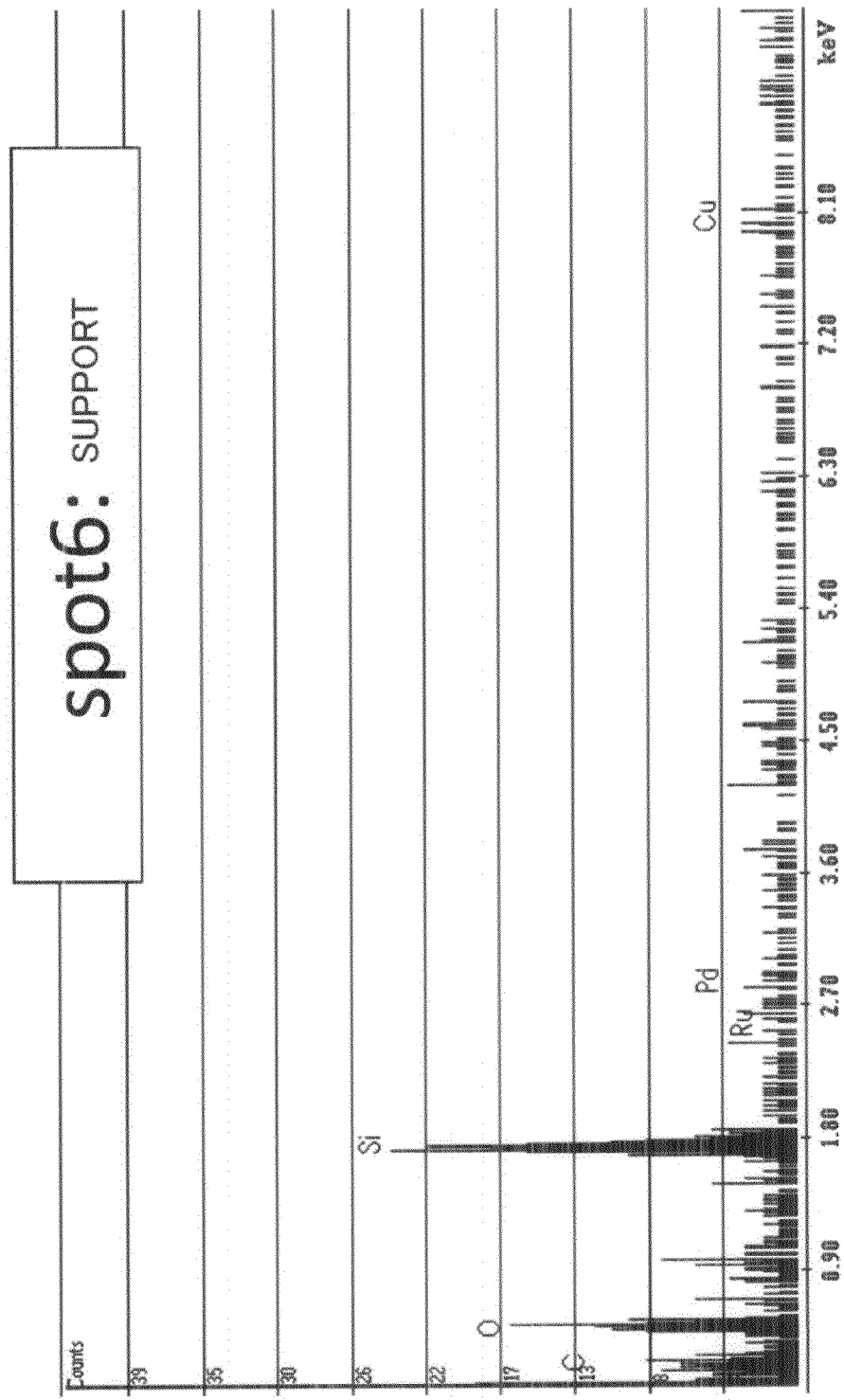
Figure 8:
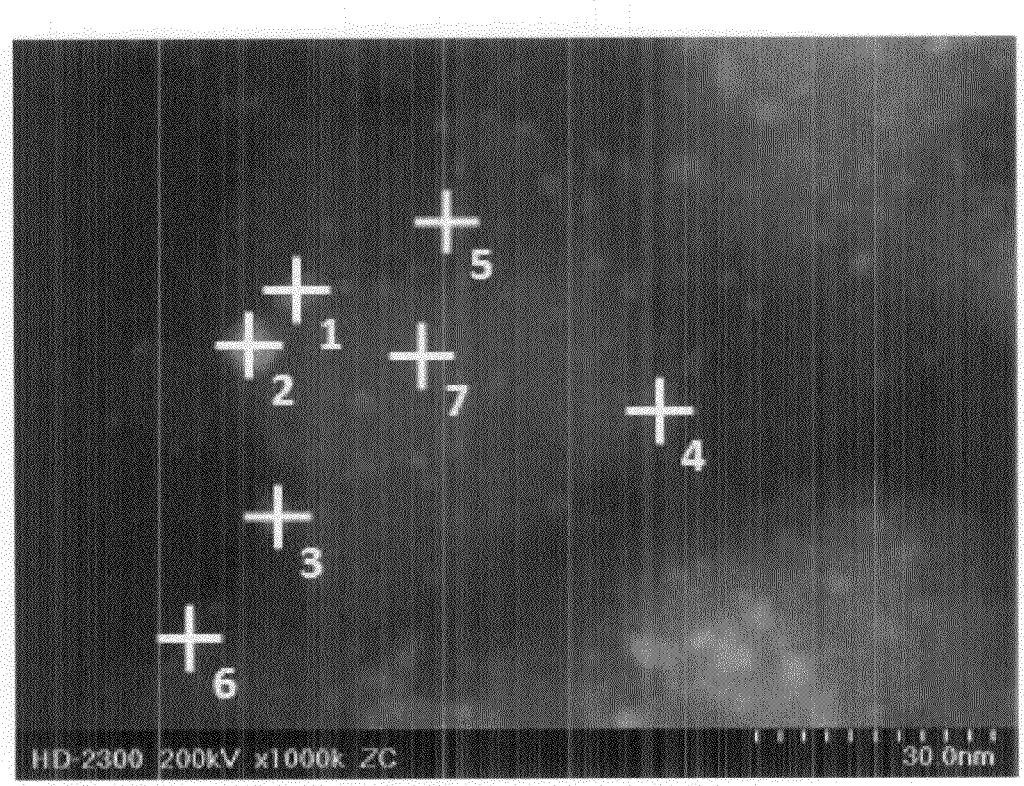
FIG. 8(1) shows EDX analysis results of particles observed in a transmission electron microscopic image of the co-supported ruthenium-palladium catalyst produced in Example 22.
Figure 8:
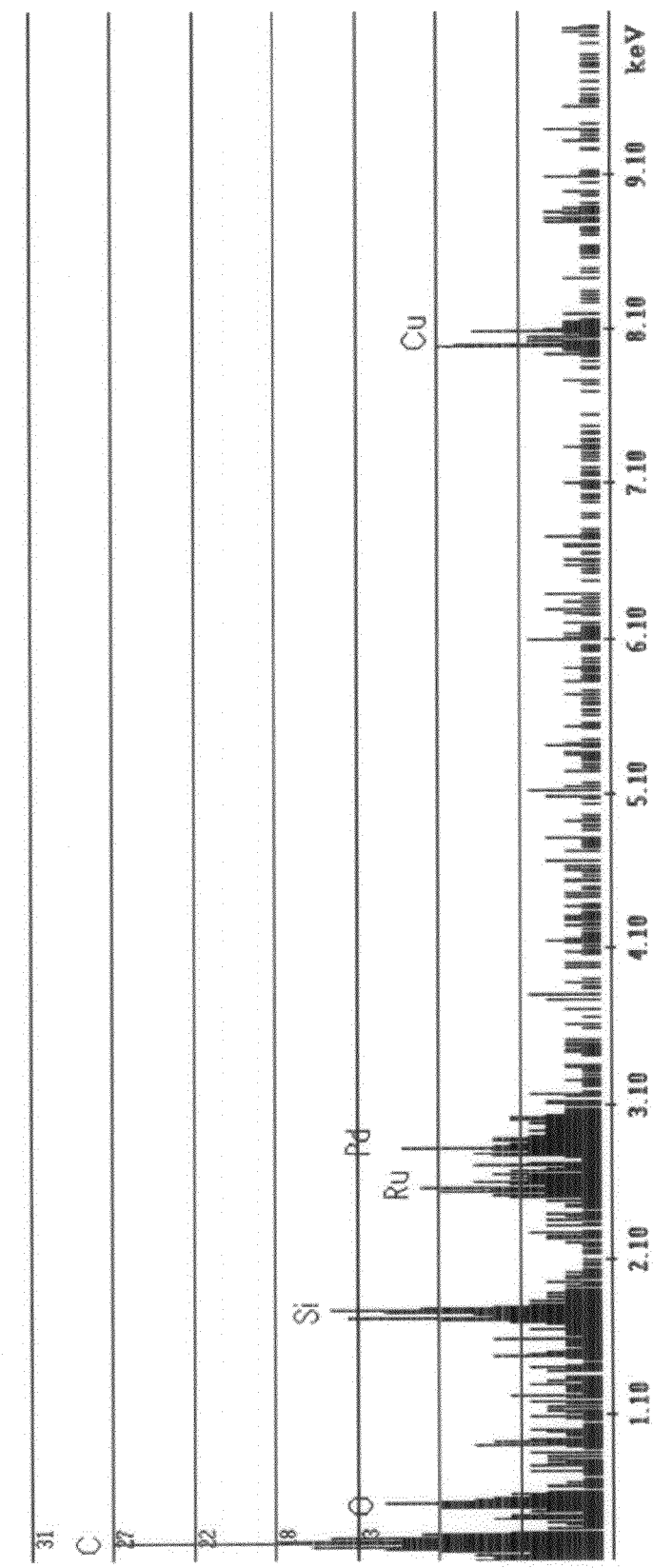
Figure 8:
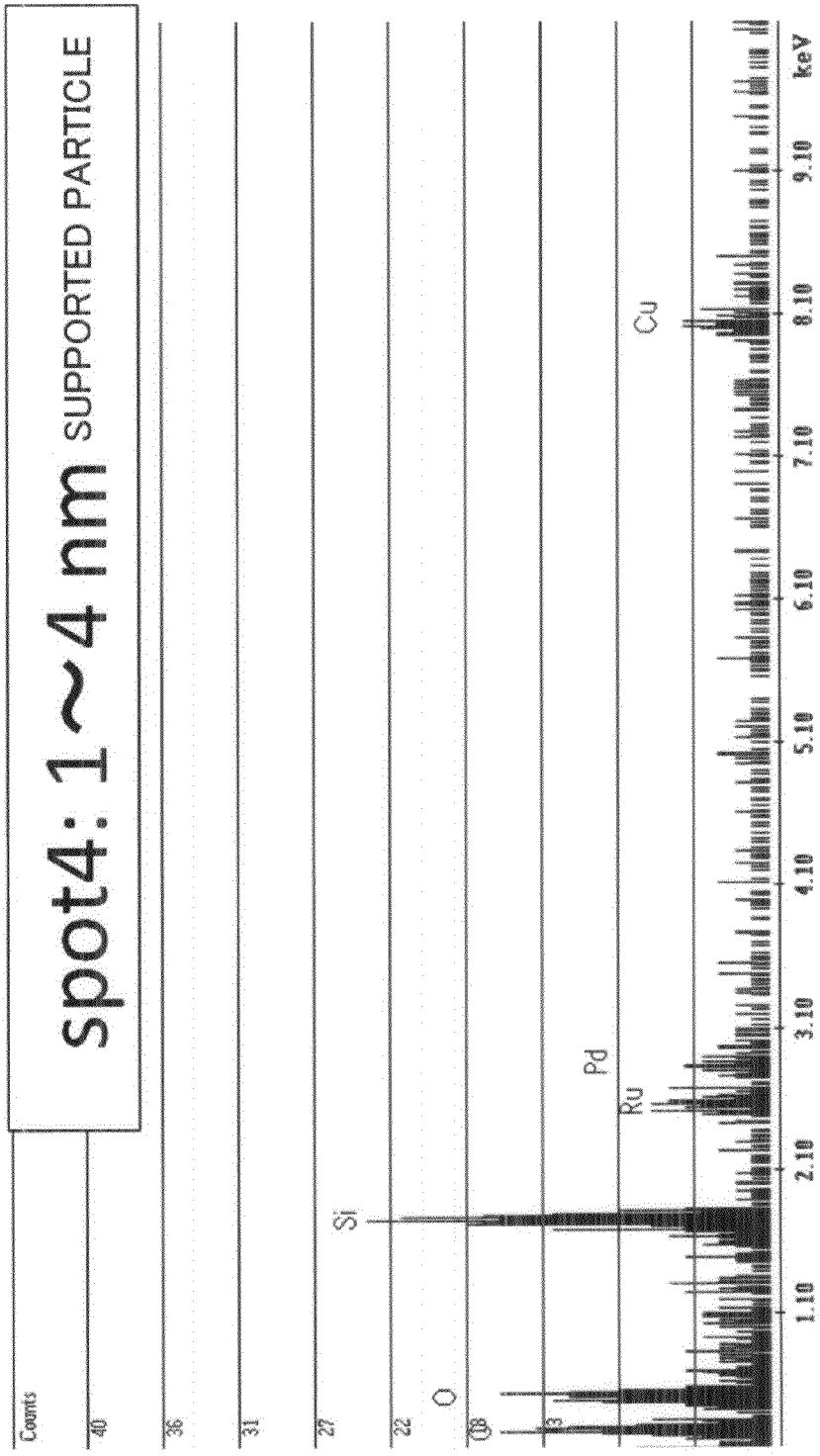
Figure 8:
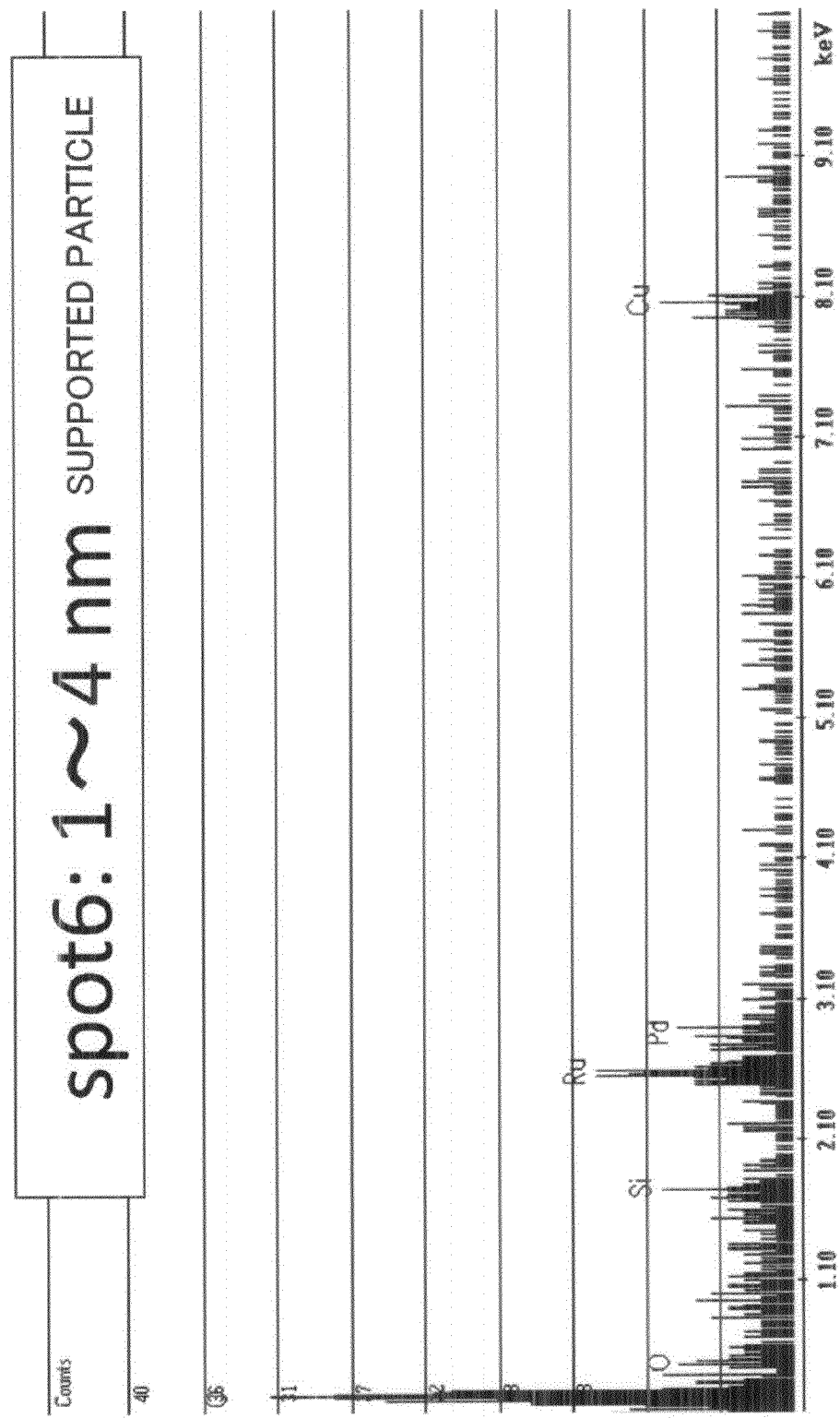

FIGS. 3 and 4 show transmission electron microscopic images of the co-supported ruthenium-palladium catalyst prepared by this method. The sizes of particles present on the surface of the support were 1 to 15 nm. FIGS. 7 and 8 show EDX analysis results of coexistent states of ruthenium and palladium in the particles. The average value of the molar ratios of ruthenium and palladium contained in the particles was 1.

Example 23

In water, 0.323 g of ruthenium chloride n-hydrate (manufactured by Wako Pure Chemical Industries, Ltd.) and 0.208 g of palladium chloride (manufactured by Wako Pure Chemical Industries, Ltd.) were dissolved. To 5 g of titania (manufactured by Wako Pure Chemical Industries, Ltd.), water and 1 g of NaOH (manufactured by Wako Pure Chemical Industries, Ltd.) were added, so that the total weight was adjusted to 100 g, and the mixture was heated in a water bath. After the temperature of the aqueous solution was raised to about 80° C., the aqueous solution containing ruthenium chloride and palladium chloride was added over 60 minutes. After about 60 minutes had elapsed from the completion of the addition, the mixture was cooled, and a co-supported ruthenium-palladium catalyst (2.5% by weight Ru-2.5% by weight Pd/$TiO_2$) was collected by filtration.

Example 24

Into a 200-ml SUS-316 autoclave, 6 g of trimellitic acid (manufactured by Tokyo Chemical Industry Co., Ltd.), 1.2 g of a 2.5% by weight Ru-2.5% by weight Pd/silica catalyst prepared by the method described in Example 21, and 36 g of water were introduced. The pressure was raised to 9 MPa with hydrogen, and the temperature was raised to 50° C., with stirring using a magnetic stirring impeller. Absorption of hydrogen stopped in 2.0 hours from the start of the temperature raise, which indicated the completion of the reaction. The reaction product was converted to a methyl ester derivative, and then analyzed by gas chromatography. The conversion of trimellitic acid was 100%, and the selectivity to hydrogenated trimellitic acid (1,2,4-cyclohexanetricarboxylic acid) was 94.1% by mole.

Example 25

Into a 200-ml SUS-316 autoclave, 5 g of trimellitic acid (manufactured by Tokyo Chemical Industry Co., Ltd.), 0.5 g of a 2.5% by weight Ru-2.5% by weight Pd/silica catalyst prepared by the method described in Example 22, and 60 g of water were introduced. The pressure was raised to 9 MPa with hydrogen, and the temperature was raised to 50° C., with stirring using a magnetic stirring impeller. Absorption of hydrogen stopped in 1.0 hour from the start of the temperature raise, which indicated the completion of the reaction. The reaction product was converted to a methyl ester derivative, and then analyzed by gas chromatography. The conversion of trimellitic acid was 100%, and the selectivity to hydrogenated trimellitic acid was 96.6% by mole.

Example 26

Into a 200-ml SUS-316 autoclave, 6 g of trimellitic acid (manufactured by Tokyo Chemical Industry Co., Ltd.), 1.2 g of a 2.5% by weight Ru-2.5% by weight Pd/titania powder catalyst prepared by the method described in Example 23, and 36 g of water were introduced. The pressure was raised to 9 MPa with hydrogen, and the temperature was raised to 55° C., with stirring using a magnetic stirring impeller. Absorption of hydrogen stopped in 1.5 hours from the start of the temperature raise, which indicated the completion of the reaction. The reaction product was converted to a methyl ester derivative, and then analyzed by gas chromatography. The conversion of trimellitic acid was 100%, and the selectivity to hydrogenated trimellitic acid was 94.0% by mole.

Example 27

Into a 200-ml SUS-316 autoclave, 5 g of pyromellitic acid (manufactured by Tokyo Chemical Industry Co., Ltd.), 0.5 g of a 2.5% by weight Ru-2.5% by weight Pd/silica catalyst prepared by the method described in Example 22, and 60 g of water were introduced. The pressure was raised to 9 MPa with hydrogen, and the temperature was raised to 50° C., with stirring using a magnetic stirring impeller. Absorption of hydrogen stopped in 2.0 hours from the start of the temperature raise, which indicated the completion of the reaction. The reaction product was converted to a methyl ester derivative, and then analyzed by gas chromatography. The conversion of pyromellitic acid was 100%, and the selectivity to hydrogenated pyromellitic acid (1,2,4,5-cyclohexanetetracarboxylic acid) was 96.1% by mole.

Example 28

Into a 200-ml SUS-316 autoclave, 6 g of pyromellitic acid (manufactured by Tokyo Chemical Industry Co., Ltd.), 1.2 g of a 2.5% by weight Ru-2.5% by weight Pd/titania powder catalyst prepared by the method described in Example 23, and 36 g of water were introduced. The pressure was raised to 9 MPa with hydrogen, and the temperature was raised to 50° C., with stirring using a magnetic stirring impeller. Absorption of hydrogen stopped in 3.0 hours from the start of the temperature raise, which indicated the completion of the reaction. The reaction product was converted to a methyl ester derivative, and then analyzed by gas chromatography. The conversion of pyromellitic acid was 100%, and the selectivity to hydrogenated pyromellitic acid was 94.5% by mole.

Example 29

Into a 30-ml SUS-316 autoclave, 1.5 g of trimesic acid (manufactured by Tokyo Chemical Industry Co., Ltd.), 0.3 g of a 2.5% by weight Ru-2.5% by weight Pd/titania powder catalyst prepared by the method described in Example 23, and 9 g of water were introduced. The pressure was raised to 10 MPa with hydrogen, and the temperature was raised to 60° C., with stirring using a stirrer chip. Absorption of hydrogen stopped in 1.4 hours from the start of the temperature raise, which indicated the completion of the reaction. The reaction product was converted to a methyl ester derivative, and then analyzed by gas chromatography. The conversion of trimesic acid was 100%, and the selectivity to hydrogenated trimesic acid (1,3,5-cyclohexanetricarboxylic acid) was 93.0% by mole.

Example 30

Into a 200-ml SUS-316 autoclave, 5 g of trimesic acid (manufactured by Tokyo Chemical Industry Co., Ltd.), 0.5 g of a 2.5% by weight Ru-2.5% by weight Pd/silica catalyst prepared by the method described in Example 22, and 60 g of water were introduced. The pressure was raised to 9 MPa with hydrogen, and the temperature was raised to 50° C., with stirring using a magnetic stirring impeller. Absorption of hydrogen stopped in 1.0 hour from the start of the temperature raise, which indicated the completion of the reaction. The reaction product was converted to a methyl ester derivative, and then analyzed by gas chromatography. The conversion of trimesic acid was 100%, and the selectivity to hydrogenated trimesic acid was 96.1% by mole.

Example 31

Into a 300-ml SUS-316 autoclave, 20 g of trimellitic acid (manufactured by Tokyo Chemical Industry Co., Ltd.), 4.0 g of a 2.5% by weight Ru-2.5% by weight Pd/titania powder catalyst prepared by the method described in Example 23, and 120 g of water were introduced. The pressure was raised to 8 MPa with hydrogen, and the temperature was raised to 60° C., with stirring using a magnetic stirring impeller. Absorption of hydrogen stopped in 2.0 hours after the temperature raise to 60° C., which indicated the completion of the reaction. The reaction product was converted to a methyl ester derivative, and then analyzed by gas chromatography. The conversion of trimellitic acid was 100%, and the selectivity to hydrogenated trimellitic acid was 93.5% by mole.

The reaction was repeated under the same conditions, without activating the recovered catalyst. Up to the 7th reaction, the conversion of trimellitic acid was 100%, and the average selectivity to hydrogenated trimellitic acid was 93.6% by mole.

Example 32

Into a 300-ml SUS-316 autoclave, 15 g of trimellitic acid (manufactured by Tokyo Chemical Industry Co., Ltd.), 3.0 g of a 2.5% by weight Ru-2.5% by weight Pd/silica catalyst prepared by the method described in Example 21, and 120 g of water were introduced. The pressure was raised to 8 MPa with hydrogen, and the temperature was raised to 60° C., with stirring using a magnetic stirring impeller. Absorption of hydrogen stopped in 2.0 hours after the temperature raise to 60° C., which indicated the completion of the reaction. The reaction product was converted to a methyl ester derivative, and then analyzed by gas chromatography. The conversion of trimellitic acid was 100%, and the selectivity to hydrogenated trimellitic acid was 94.6% by mole.

The reaction was repeated under the same conditions, without activating the recovered catalyst. Up to 13th reaction, the conversion of trimellitic acid was 100%, and the average selectivity to hydrogenated trimellitic acid was 94.3% by mole.

Example 33

Into a SUS-316 reaction tube having an inner diameter of 17 mm and a length of 320 mm, 10 g (25 ml, particle diameters of 1.40 to 2.36 mm) of a 1.0% by weight Ru-1.0% by weight Pd/crushed silica catalyst prepared by the method described in Example 21 was packed. A reaction was allowed to proceed by passing an aqueous solution of 6% by weight trimellitic acid (manufactured by Tokyo Chemical Industry Co., Ltd.) at 15 g/hr and hydrogen at 0.9 L/hr under conditions of a temperature of 60° C. and a hydrogen pressure of 8 MPa. At 5500 hours from the start of the reaction, no decrease in conversion of trimellitic acid was observed, and the conversion was maintained at 99% or higher from the initial stage of the reaction. During this period, the selectivity to hydrogenated trimellitic acid stayed around 94% by mole.

Example 34

Into a 200-ml SUS-316 autoclave, 5 g of trimellitic acid (manufactured by Tokyo Chemical Industry Co., Ltd.), 0.5 g of a 2.5% by weight Ru-2.5% by weight Pd/alumina catalyst prepared by the same method as described in Example 22, and 60 g of water were introduced. The pressure was raised to 9 MPa with hydrogen, and the temperature was raised to 50° C., with stirring using a magnetic stirring impeller. Absorption of hydrogen stopped in 1.2 hours from the start of the temperature raise, which indicated the completion of the reaction. The reaction product was converted to a methyl ester derivative, and then analyzed by gas chromatography. The conversion of trimellitic acid was 100%, and the selectivity to hydrogenated trimellitic acid was 96.2% by mole.

Example 35

Into a 30-ml SUS-316 autoclave, 1.5 g of trimellitic acid (manufactured by Tokyo Chemical Industry Co., Ltd.), 0.3 g of a 2.5% by weight Ru-2.5% by weight Pd/zirconia powder catalyst prepared by the same method as described in Example 21, and 9 g of water were introduced. The pressure was raised to 10 MPa with hydrogen, and the temperature was raised to 60° C., with stirring using a stirrer chip. Absorption of hydrogen stopped in 2.0 hours from the start of the temperature raise, which indicated the completion of the reaction. The reaction product was converted to a methyl ester derivative, and then analyzed by gas chromatography. The conversion of trimellitic acid was 100%, and the selectivity to hydrogenated trimellitic acid was 94.2% by mole.

Example 36

Into a 30-ml SUS-316 autoclave, 1.5 g of trimellitic acid (manufactured by Tokyo Chemical Industry Co., Ltd.), 0.3 g of a 2.5% by weight Ru-2.5% by weight Pd/ceria powder catalyst prepared by the same method as described in Example 23, and 9 g of water were introduced. The pressure was raised to 10 MPa with hydrogen, and the temperature was raised to 60° C., with stirring using a stirrer chip. Absorption of hydrogen stopped in 1.6 hours from the start of the temperature raise, which indicated the completion of the reaction. The reaction product was converted to a methyl ester derivative, and then analyzed by gas chromatography. The conversion of trimellitic acid was 100%, and the selectivity to hydrogenated trimellitic acid was 92.7% by mole.

Example 37

Into a 30-ml SUS-316 autoclave, 1.0 g of trimellitic acid (manufactured by Tokyo Chemical Industry Co., Ltd.), 0.5 g of a 1.0% by weight Ru-4.0% by weight Pd/carbon powder catalyst prepared by the same method as described in Example 23, and 10 g of water were introduced. The pressure was raised to 10 MPa with hydrogen, and the temperature was raised to 60° C., with stirring using a stirrer chip. Absorption of hydrogen stopped in 0.5 hours from the start of the temperature raise, which indicated the completion of the reaction. The reaction product was converted to a methyl ester derivative, and then analyzed by gas chromatography. The conversion of trimellitic acid was 100%, and the selectivity to hydrogenated trimellitic acid was 98.6% by mole.

Example 38

Into a 30-ml SUS-316 autoclave, 1.0 g of trimellitic acid (manufactured by Tokyo Chemical Industry Co., Ltd.), 0.5 g of a 2.5% by weight Ru-2.5% by weight Pd/carbon powder catalyst prepared by the same method as described in Example 23, and 10 g of water were introduced. The pressure was raised to 10 MPa with hydrogen, and the temperature was raised to 60° C., with stirring using a stirrer chip. Absorption of hydrogen stopped in 0.5 hours from the start of the temperature raise, which indicated the completion of the reaction. The reaction product was converted to a methyl ester derivative, and then analyzed by gas chromatography. The conversion of trimellitic acid was 100%, and the selectivity to hydrogenated trimellitic acid was 96.9% by mole.

Example 39

Into a 30-ml SUS-316 autoclave, 1.0 g of trimellitic acid (manufactured by Tokyo Chemical Industry Co., Ltd.), 0.5 g of a 4.0% by weight Ru-1.0% by weight Pd/carbon powder catalyst prepared by the same method as described in Example 23, and 10 g of water were introduced. The pressure was raised to 10 MPa with hydrogen, and the temperature was raised to 60° C., with stirring using a stirrer chip. Absorption of hydrogen stopped in 0.6 hours from the start of the temperature raise, which indicated the completion of the reaction. The reaction product was converted to a methyl ester derivative, and then analyzed by gas chromatography. The conversion of trimellitic acid was 100%, and the selectivity to hydrogenated trimellitic acid was 97.2% by mole.

Comparative Example 22

Into a 300-ml SUS-316 autoclave, 20 g of trimellitic acid (manufactured by Tokyo Chemical Industry Co., Ltd.), 3.2 g of a 5.0% by weight Pd/alumina powder catalyst (manufactured by N.E. CHEMCAT Corporation), and 120 g of water were introduced. The pressure was raised to 10 MPa with hydrogen, and the temperature was raised to 100° C., with stirring using a magnetic stirring impeller. Although the absorption of hydrogen continued even after 14.0 hours had elapsed from the temperature raise to 100° C., the reaction was stopped. The reaction product was converted to a methyl ester derivative, and then analyzed by gas chromatography. The conversion of trimellitic acid was 11.8%, and the selectivity to hydrogenated trimellitic acid was 30.2% by mole.

Comparative Example 23

Into a 200-ml SUS-316 autoclave, 5 g of trimellitic acid (manufactured by Tokyo Chemical Industry Co., Ltd.), 0.5 g of a 2.5% by weight Ru/silica powder catalyst prepared by the same method as described in Example 21, and 60 g of water were introduced. The pressure was raised to 8 MPa with hydrogen, and the temperature was raised to 100° C., with stirring using a magnetic stirring impeller. Although the absorption of hydrogen continued even after 2 hours had elapsed from the temperature raise to 100° C., the reaction was stopped. The reaction product was converted to a methyl ester derivative, and then analyzed by gas chromatography. The conversion of trimellitic acid was 54.9%, and the selectivity to hydrogenated trimellitic acid was 82.7% by mole.

Comparative Example 24

Into a 200-ml SUS-316 autoclave, 5 g of trimellitic acid (manufactured by Tokyo Chemical Industry Co., Ltd.), 0.5 g of a 2.5% by weight Pd/silica powder catalyst prepared by the same method as described in Example 22, and 60 g of water were introduced. The pressure was raised to 9 MPa with hydrogen, and the temperature was raised to 50° C., with stirring using a magnetic stirring impeller. Although the absorption of hydrogen continued even after 2 hours had elapsed from the temperature raise to 50° C., the reaction was stopped. The reaction product was converted to a methyl ester derivative, and then analyzed by gas chromatography. The conversion of trimellitic acid was 6.7%, and the selectivity to hydrogenated trimellitic acid was 69.8% by mole.

Comparative Example 25

Into a 200-ml SUS-316 autoclave, 5 g of trimellitic acid (manufactured by Tokyo Chemical Industry Co., Ltd.), 0.5 g of a 2.5% by weight Ru/silica powder catalyst prepared by the same method as described in Example 21, 0.5 g of a 2.5% by weight Pd/silica powder catalyst prepared by the same method as described in Example 22, and 60 g of water were introduced. The pressure was raised to 9 MPa with hydrogen, and the temperature was raised to 50° C., with stirring using a magnetic stirring impeller. Although the absorption of hydrogen continued even after 2 hours had elapsed from the temperature raise to 50° C., the reaction was stopped. The reaction product was converted to a methyl ester derivative, and then analyzed by gas chromatography. The conversion of trimellitic acid was 17.2%, and the selectivity to hydrogenated trimellitic acid was 86.2% by mole.

Comparative Example 26

Into a 30-ml SUS-316 autoclave, 1.0 g of trimellitic acid (manufactured by Tokyo Chemical Industry Co., Ltd.), 0.25 g of a 5.0% by weight Ru/carbon powder (manufactured by N.E. CHEMCAT Corporation), 0.25 g of a 5.0% by weight Pd/carbon powder (manufactured by N.E. CHEMCAT Corporation), and 10 g of water were introduced. The pressure was raised to 10 MPa with hydrogen, and the temperature was raised to 60° C., with stirring using a stirrer chip. Although the absorption of hydrogen continued even after 3 hours had elapsed from the start of the temperature raise, the reaction was stopped. The reaction product was converted to a methyl ester derivative, and then analyzed by gas chromatography. The conversion of trimellitic acid was 88.0%, and the selectivity to hydrogenated trimellitic acid was 93.0% by mole.

Comparative Example 27

Into a 30-ml SUS-316 autoclave, 1.5 g of trimellitic acid (manufactured by Tokyo Chemical Industry Co., Ltd.), 0.15 g of a 2.5% by weight Ru/titania powder catalyst prepared by the same method as described in Example 23, 0.15 g of a 2.5% by weight Pd/titania powder catalyst prepared by the same method as described in Example 23, and 9 g of water were introduced. The pressure was raised to 10 MPa with hydrogen, and the temperature was raised to 60° C., with stirring using a stirrer chip. Although the absorption of hydrogen continued even after 3 hours had elapsed from the start of the temperature raise, the reaction was stopped. The reaction product was converted to a methyl ester derivative, and then analyzed by gas chromatography. The conversion of trimellitic acid was 49%, and the selectivity to hydrogenated trimellitic acid was 87.0% by mole.

Comparative Example 28

Into a 30-ml SUS-316 autoclave, 1.0 g of trimellitic acid (manufactured by Tokyo Chemical Industry Co., Ltd.), 0.5 g of a 2.5% by weight Ru-2.5% by weight Pt/carbon powder catalyst prepared by the same method as described in Example 23, and 10 g of water were introduced. The pressure was raised to 10 MPa with hydrogen, and the temperature was raised to 60° C., with stirring using a stirrer chip. Although the absorption of hydrogen continued even after 3 hours had elapsed from the start of the temperature raise, the reaction was stopped. The reaction product was converted to a methyl ester derivative, and then analyzed by gas chromatography. The conversion of trimellitic acid was 25.0%, and the selectivity to hydrogenated trimellitic acid was 88.0% by mole.

Comparative Example 29

Into a 30-ml SUS-316 autoclave, 1.0 g of trimellitic acid (manufactured by Tokyo Chemical Industry Co., Ltd.), 0.5 g of a 2.5% by weight Ru-2.5% by weight Ir/carbon powder catalyst prepared by the same method as described in Example 23, and 10 g of water were introduced. The pressure was raised to 10 MPa with hydrogen, and the temperature was raised to 60° C., with stirring using a stirrer chip. Although the absorption of hydrogen continued even after 3 hours had elapsed from the start of the temperature raise, the reaction was stopped. The reaction product was converted to a methyl ester derivative, and then analyzed by gas chromatography. The conversion of trimellitic acid was 10.0%, and the selectivity to hydrogenated trimellitic acid was 78.4% by mole.

Comparative Example 30

Into a 30-ml SUS-316 autoclave, 1.0 g of trimellitic acid (manufactured by Tokyo Chemical Industry Co., Ltd.), 0.5 g of a 2.5% by weight Pd-2.5% by weight Pt/carbon powder catalyst prepared by the same method as described in Example 23, and 10 g of water were introduced. The pressure was raised to 10 MPa with hydrogen, and the temperature was raised to 60° C., with stirring using a stirrer chip. Although the absorption of hydrogen continued even after 3 hours had elapsed from the start of the temperature raise, the reaction was stopped. The reaction product was converted to a methyl ester derivative, and then analyzed by gas chromatography. The conversion of trimellitic acid was 45.0%, and the selectivity to hydrogenated trimellitic acid was 96.7% by mole.

Comparative Example 31

Into a 30-ml SUS-316 autoclave, 1.0 g of trimellitic acid (manufactured by Tokyo Chemical Industry Co., Ltd.), 0.5 g of a 2.5% by weight Pd-2.5% by weight Ir/carbon powder catalyst prepared by the same method as described in Example 23, and 10 g of water were introduced. The pressure was raised to 10 MPa with hydrogen, and the temperature was raised to 60° C., with stirring using a stirrer chip. Although the absorption of hydrogen continued even after 3 hours had elapsed from the start of the temperature raise, the reaction was stopped. The reaction product was converted to a methyl ester derivative, and then analyzed by gas chromatography. The conversion of trimellitic acid was 14.0%, and the selectivity to hydrogenated trimellitic acid was 89.4% by mole.

Comparative Example 32

Into a 30-ml SUS-316 autoclave, 1.0 g of trimellitic acid (manufactured by Tokyo Chemical Industry Co., Ltd.), 0.5 g of a 2.5% by weight Pd-2.5% by weight Au/carbon powder catalyst prepared by the same method as described in Example 21, and 10 g of water were introduced. The pressure was raised to 10 MPa with hydrogen, and the temperature was raised to 60° C., with stirring using a stirrer chip. Although the absorption of hydrogen continued even after 3 hours had elapsed from the start of the temperature raise, the reaction was stopped. The reaction product was converted to a methyl ester derivative, and then analyzed by gas chromatography. The conversion of trimellitic acid was 76.0%, and the selectivity to hydrogenated trimellitic acid was 96.2% by mole.

Comparative Example 33

Into a 200-ml SUS-316 autoclave, 6 g of trimellitic acid (manufactured by Tokyo Chemical Industry Co., Ltd.), 1.2 g of a 2.5% by weight Ru-2.5% by weight Pt/titania powder catalyst prepared by the same method as described in Example 23, and 36 g of water were introduced. The pressure was raised to 9 MPa with hydrogen, and the temperature was raised to 60° C., with stirring using a magnetic stirring impeller. Although the absorption of hydrogen continued even after 2 hours had elapsed from the start of the temperature raise, the reaction was stopped. The reaction product was converted to a methyl ester derivative, and then analyzed by gas chromatography. The conversion of trimellitic acid was 42%, and the selectivity to hydrogenated trimellitic acid was 89.7% by mole.

Comparative Example 34

Into a 200-ml SUS-316 autoclave, 5 g of trimellitic acid (manufactured by Tokyo Chemical Industry Co., Ltd.), 0.5 g of a 2.5% by weight Pd-2.5% by weight Pt/silica powder catalyst prepared by the same method as described in Example 21, and 60 g of water were introduced. The pressure was raised to 9 MPa with hydrogen, and the temperature was raised to 50° C., with stirring using a magnetic stirring impeller. Although the absorption of hydrogen continued even after 2 hours had elapsed from the temperature raise to 50° C., the reaction was stopped. The reaction product was converted to a methyl ester derivative, and then analyzed by gas chromatography. The conversion of trimellitic acid was 10.5%, and the selectivity to hydrogenated trimellitic acid was 83.9% by mole.

Comparative Example 35

Into a 300-ml SUS-316 autoclave, 20 g of trimellitic acid (manufactured by Tokyo Chemical Industry Co., Ltd.), 1.6 g of a 5.0% by weight Rh/carbon powder catalyst (manufactured by N.E. CHEMCAT Corporation), and 120 g of water were introduced. The pressure was raised to 8 MPa with hydrogen, and the temperature was raised to 40° C., with stirring using a magnetic stirring impeller. Absorption of hydrogen stopped in 4.0 hours after the temperature raise to 40° C., which indicated the completion of the reaction. The reaction product was converted to a methyl ester derivative, and then analyzed by gas chromatography. The conversion of trimellitic acid was 100%, and the selectivity to hydrogenated trimellitic acid was 97.2% by mole. The reaction was repeated under the same conditions, without activating the recovered catalyst. However, no absorption of hydrogen was observed, and the conversion of trimellitic acid was 0%.

What is claimed is:

1. A method for producing an alicyclic carboxylic acid, the method comprising:
   hydrogenating an aromatic ring of an aromatic carboxylic acid in the presence of a catalyst in water,
   wherein the aromatic carboxylic acid is selected from the group consisting of trimellitic acid, trimesic acid and pyromellitic acid; and
   the catalyst is a catalyst in which ruthenium and palladium are co-supported on a support.

2. The method according to claim 1,
   wherein the support is at least one selected from the group consisting of activated carbon, alumina, zirconia, ceria, titania, and silica.

3. The method according to claim 1,
   wherein the catalyst a co-supported ruthenium-palladium catalyst in which the ruthenium and the palladium are present in a form of particles comprising both the ruthenium and the palladium on a surface of the support.

4. The method according to claim 1,
   wherein the aromatic carboxylic acid is present in an amount of from 1 to 50% by weight of the total amount of the aromatic carboxylic acid and the water.

5. The method according to claim 1,
   wherein the total amount of the ruthenium and the palladium is from 0.5 to 10% by weight of the total amount of the aromatic carboxylic acid and the water.

\* \* \* \* \*